US006537754B1

United States Patent
Gudkov et al.

(10) Patent No.: US 6,537,754 B1
(45) Date of Patent: Mar. 25, 2003

(54) ASSOCIATION OF KINESIN WITH SENSITIVITY TO CHEMOTHERAPEUTIC DRUGS

(75) Inventors: Andrei Gudkov, Chicago; Igor B. Roninson, Wilmette, both of IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/535,789

(22) Filed: Mar. 28, 2000

Related U.S. Application Data

(60) Division of application No. 09/235,546, filed on Jan. 22, 1999, now Pat. No. 6,043,340, which is a division of application No. 08/486,382, filed on Jun. 7, 1995, now Pat. No. 5,866,327, which is a continuation of application No. 08/177,571, filed on Jan. 5, 1994, now abandoned, which is a continuation-in-part of application No. 08/033,086, filed on Mar. 3, 1993, which is a continuation-in-part of application No. 08/039,385, filed as application No. PCT/US91/07492 on Oct. 11, 1991, now Pat. No. 5,811,234, which is a continuation-in-part of application No. 07/599,730, filed on Oct. 19, 1990, now Pat. No. 5,217,889.

(51) Int. Cl.$^7$ .......................... C12Q 1/68; G01N 33/53; G01N 33/48; G01N 33/00; C12P 21/64
(52) U.S. Cl. .......................... 435/6; 435/7.1; 435/91.3; 435/70.1; 435/70.3; 436/63; 436/64; 436/94; 436/86
(58) Field of Search ........................ 435/6, 7.1, 91.3, 435/70.1, 70.3; 436/63, 64, 94, 86

(56) References Cited

U.S. PATENT DOCUMENTS 5,217,889 A 6/1993 Roninson

OTHER PUBLICATIONS

Baltimore, Nature 335: 395–396 (1988).
Bunnell et al., Somat. Cell Mol. Genet. 16: 151–162 (1990).
Ch'ng et al., Proc. Natl. Acad. Sci. 86: 10006–10010 (1989).
Chejanovsky et al., J. Virol. 64: 1764–1770 (1990).
Eliyahu et al., 1984, Nature 312: 646–659.
Fereira et al., J. Cell Biol 117:595–606 (1992).
Graf & Beug, 1983, Cell 34: 7–9.
Kerr et al., Eur. J. Biochem 175:65–73 (1998).
Lau and Nathans Proc. Natl. Acad. Sci USA 84:1182–1186 (1987).
Lee et al., J. Bacteriol 171:3002–3007 (1989).
Liu et al., 1992, Antivir. Res. 19: 247–265.
Markowitz et al., Virology 167: 400–406 (1988).
McConkey et al., 1989, Arch. Biochem. Biophys. 269:365–370.
Powell et al., Proc. Natl. Acad. Sci, USA 86: 6949–6952 (1989).
Forchhammer et al. Proc. Natl Acad Sci USA 84:1182–1186 (1987).
Ransone et al., Proc. Natl. Acad. Sci. USA 87:3806–3810 (1990).
Sarver et al., Science 247:1222–1225 (1990).
Whitaker–Dowling et al., Virology 175:358–364 (1990).
Stearns et al. Regulation of kinesin expression and type IV collagenase secretion in invasive human prostate PC–3 tumor sublines. Cancer Res. 51 (11/1991): 5866–5875.*
Albritton et al., 1989, Cell 57:659–666.
Altshul et al., 1990, J. Mol. Biol. 215:403–410.
Baim et al. Proc Natl Acad Sci USA 88:5072–5076 (1991).
Baird et al., J. Bacteriol 172: 1587–1594 (1990).
Ballester et al., 1990, Cell 62: 851–859.
Barbacid, 1987, Ann. Rev. Biochem. 56: 779–827.
Bender et al., 1987, J. Virol 61: 1639–1646.
Bodine et al Proc Natl Acad Sci USA 87:3738–3742 (1990).
Buchberg et al., 1990, Nature 347:291–294.
Call et al., 1990, Cell 60: 509–520.
Chen et al. Cell 47:381–389 (1986).
Culver et al. Science 256:1550–1552 (1992).
Damm et al., 1987, EMBO J. 6: 375–382.
Damm et al., 1989, Nature 339: 593–597.
Daugherty et al., Gene Anal. Tech. 6:1–16 (1989).
Deiss et al., Science vol. 252:117–120 (1991).
Duerre et al., 1992, Biochem. Biolog. Cell. 70:703–711.
Endow, Trends Biochem Scie 16: 221–225 (1991).
Fearon et al., 1990, Science 247: 49–56.
Fields et al., 1990 Science, 249:1046–1049.
Finlay et al., 1988, Molec. Cell Biol. 8: 531–539.
Friedman et al., Nature 355:452–454 (1988).
Friend et al., 1987, Proc. Natl. Acad. Sci. USA 84:9059–9063.
Gessler et al., 1990, Nature 343: 774–778.
Groger et al., Gene 81: 285–294 (1989).
Gudkov et al., 1993, Proc. Natl. Acad. Sci. USA 90: 3231–3235.
Gussow et al., J. Immunol. 139: 3132–3138 (1987).
Herskowitz, Nature, 329:219–22(1987).
Holzmayer et al. Nucleic Acids Res 20: 711–717 (1992).
Hunter, 1991, Cell 64: 249–270.
Keown et al., Methods Enzymol 185: 527–536 (1990).
Kern et al., 1991, Oncogene 6: 131–136.
Kern et al., 1991, Science 252: 1708–1711.

(List continued on next page.)

*Primary Examiner*—Andrew Wang
*Assistant Examiner*—Karen A Lacourciere
(74) *Attorney, Agent, or Firm*—McDonnell Boehnen Hulbert & Berghoff

(57) ABSTRACT

The invention provides diagnostic assays for assessing the sensitivity or resistance to DNA damaging agents and microtubule-directed chemotherapeutic drugs of malignant cells in a tumor or tissue. The assay provided involves determining gene expression levels of kinesin genes in the malignant cells, wherein under-expression of kinesin is found in cells resistant to DNA damaging agents and sensitive to microtubule-directed chemotherapeutic drugs, and over-expression of kinesin is found in cells sensitive to DNA damaging agents and resistant to microtubule-directed chemotherapeutic drugs.

8 Claims, 36 Drawing Sheets

OTHER PUBLICATIONS

Kidd V.J. et al., Chemical Abstracts 111(23).
Kim et al., J. Biol. Chem. 267: 23113–23121.
Kinzler et al., 1987, Science 236: 70–73.
Kozak and Kabat, J. Virol 64 3500–3508 (1990).
Kosik et al., J. Biol. Chem. 265: 3278–3283 (1990).
Kung et al., 1990, Cancer Res. 50:7307–7317.
Laforgia et al., 1991, Proc. Natl. Acad. Sci. USA 88: 5036–5040.
Lau and Nathans, EMBO J. 4:3145–3151 (1985).
Lee et al., 1987, Nature 329: 642–645.
Lock et al., J. Cancer 42(3): 371–381(1988).
Miller & Rosman, Biotechniques 7:980–986 (1989).
Milner et al., 1991, Molec. Cell. Biol. 11: 12–19.
Montenarh & Quasier, 1989, Oncogene 4: 379–382.
Murphy & Schmike Nucleic Acids Res. 19: 3403–3408 (1991).
Murphy and Efstatiadis, Proc. Natl. Acad. Sci. USA 84:8277–8281.
Nakatani et al., Jpn. J. Cancer Res. 81: 707–710.
Napoli C., The Plant Cell 2(4):279–289(1990).
Navone et al. J Cell Bio 117: 1263–1275 (1992).
Noonan et al Proc Natl Acad Sci USA 87:7160–7164 (1990).
O'Rourke et al., 1990, Oncogene 5:1829–1832.
Ohara et al., Proc. Natl. Acad. Sci. USA 86:5673–5677 (1989).
Parada et al., 1984, Nature 312: 649–651.
Patanjali et al., Proc. Natl. Acad. Sci. USA 88:1943–1947(1991).
Patterson et al., Methods Enzymol 151:121 (1982).
Pauwels et al., 1988, J. Virol. Meth. 20: 309–321.
Perlaky et al., 1992, Cancer Res. 52: 428–436.
Raycroft et al., 1990, Science 249: 1049–1951.
Rio et al., Science 227:23–28 (1985).
Sap et al., 1986, Nature 324: 635–640.
Sap et al., 1989, Nature, 340:242–244.
Schneider & Benner, Tethrahedron Letters 31:335 (1990).
Schwab et al., 1989, 1989, Oncogene 4:139–144.
Sczakiel G. et al., Bioch. Biophys. Res. Comm. 169(2):643–651 (1990).
Shen et al., Science 232: 643–645 (1986).
Shih et al., 1979, Proc. Natl. Acad Sci. USA 76:5714–5718.
Solomon et al., 1991, Science, 254: 1153–1160.
Trent et al., 1989, Cancer Res. 49: 420–423.
Trono et al., Cell 59:113–120 (1989).
Tsai–Pflugfleder et al. Proc. Natl. Acad. Sci. USA 85:7177–7181 (1988).
Uhlmann and Peyman Chemical Reviews 90: 543–584 (1990).
Vale, 1987, Ann. Rev. Cell Biol. 3:347–378.
van der Krol et al., Biotechniques 6:958–976 (1988).
Viskochil et al, 1990, Cell 62: 187–192.
Vogelstein et al., 1988, N. Engl. J. Med. 319:525–532.
Vogelstein et al., 1993 vol. 9 No. 4 pp. 138–141.
Weinberg 1991, Science 254:1138–1146.
Weinberger et al., 1986, Nature 324: 641–646.
Wolos et al., 1993, J. Immunol, 150:3264–3273.
Xu et al., 1990, Cell 62: 599–608.

* cited by examiner

RANDOM FRAGMENTATION control          infection

FIG. 6

```
CTTGATCCCT TCTGGTTGAT GCCAGAAGCT CTTCCTGATC CAGCATTTGT ATCTTCAATT   60
TCTCTACCAA TTGGCTTTGT TGGTTAATCT CTTCATCCTT GTCATCAAGT TGTTTATACA  120
ATTTAGCAAG TTCTTCTTCA CACTTTCTTC TTTCAGCATC GGTAAAACTA CCAGCCATTC  180
CGACTGCAGC AGCTGGTTTA TCACTGGTAA TAGCAATATC TTTATCCGCT GTGAAGGCTT  240
CCAAATTAGC TTTCTCTTTG TCAAACTGCT CATCAATAGG CACTGTCTCC CCGTTACGCC  300
AACGGTTTAG CTCGTTTTCC AGCCACT                                     327
```

FIG. 7A

```
CGACAAACAT CATCTGGGAA GACCCACACG ATGGAGGGTA AACTTCATGA TCCAGAAGGC    60
ATGGGAATTA TTCCAAGAAT AGTGCAAGAT ATTTTTAATT ATATTTACTC CATGGATGAA   120
AATTTGGAAT TTCATATATTAA GGTTTCATAT TTTGAAATAT ATTTGGATAA GATAAGGGAC   180
TTGTTAGATG TTTCAAAGAC TAACCTTTCA GTCCATGAAG ACAAAAACCG TGTTCCCTAT   240
GTAAAGGGGT GCACAGAACG TTTCGTGTGT AGTCCAGATG AAGTCATGGA TACCATAGAT   300
GAAGGGAAAT CCAACAGAGA TGTCGCAGTT ACAAATATGA ATGAACATAG CTCTAGGAGC   360
CACAGCATAT TTCTTATTAA TGTAAAACAA GAGAATACAC AAACGGAACA GAAACTCAGT   420
GGAAAGCTTT ATCTGGTTGA TTTAGCTGGC AGTGAGAAGG TTAGTAAGAC TGGGGCTGAA   480
GGTGCTGTGC TGGATGAAGC TAAGAACATC AAGAAGTCAC TTTCTGCACT TGGAAATGTC   540
ATTTCTGCTT TGGCAGAGGG CAGTACCTAT GTTCCCTATC GAGATAGTAA AATGACCAGA   600
ATTCTTCAAG ATTCATTAGG TGGCAACTGT AGGACCACTA TTGTCATATG CTGCTCTCCA   660
TCATCATACA ATGAGTCTGA GACAAAGTCA ACACTCCTCT TTGGTCAAAG GGCCAAAACA   720
ATTAAGAACA CAGTCTGTGT CAATGTAGAG TTAACTGCAG AGCAGTGGAA AAAGAAGTAT   780
```

FIG. 7B

| | | | | | |
|---|---|---|---|---|---|
| GAAAAAGAAA | AGGAAAAAAA | TAAGACTCTA | CGGAACACTA | TTCAGTGGCT | GGAAAACGAG | 840
| CTAAACCGTT | GGCGTAACGG | GGAGACAGTG | CCTATTGATG | AGCAGTTTGA | CAAAGAGAAA | 900
| GCTAATTTGG | AAGCCTTCAC | AGCGGATAAA | GATACTGCTA | TTACCAGTGA | TAAACCAGCT | 960
| GCTGCAGTCG | GAATGGCTGG | TAGTTTTACC | GATGCTGAAA | GAAGAAAGTG | TGAAGAAGAA | 1020
| CTTGCTAAAT | TGTATAAACA | GCTTGATGAC | AAGGATGAAG | AGATTAACCA | ACAAAGCCAA | 1080
| TTGGTAGAGA | AATTGAAGAC | ACAAATGCTG | GATCAGGAAG | AGCTTCTGGC | ATCAACCAGA | 1140
| AGGGATCAAG | ATAATATGCA | AGCTGAACTG | AATCGCCTCC | AAGCAGAAAA | TGATGCTTCT | 1200
| AAAGAAGAAG | TCAAAGAAGT | TTTACAGGCC | TTAGAGGAAC | TGGCTGTTAA | TTATGATCAG | 1260
| AAGTCTCAGG | AAGTTGAAGA | CAAAACAAAG | GAATATGAAT | TGCTTAGTGA | TGAATTGAAT | 1320
| CAAAAATCTG | CAACTTTAGC | AAGTATTGAT | GCTGAGCTTC | AGAAGCTGAA | GGAAATGACC | 1380
| AACCACCAGA | AGAAACGAGC | AGCTGAAATG | ATGGCATCAT | TATTAAAAGA | CCTTGCAGAA | 1440
| ATAGGAATTG | CTGTGGGGAA | TAACGATGTG | AAGCAACCAG | AAGGAACTGG | TATGATAGAT | 1500
| GAAGAGTTTA | CTGTTGCAAG | ACTCTACATT | AGCAAAAATGA | AATCAGAAGT | AAAGACCATG | 1560

FIG. 7C

```
GTGAAACGCT GCAAACAGCT AGAAAGCACG CAGACTGAGA GCAACAAAAA AATGGAAGAA   1620
AATGAGAAAG AGTTAGCAGC ATGCCAGCTT CGGATCTCCC AACATGAAGC CAAAATCAAG   1680
TCACTGACTG AGTACCTTCA GAATGTAGAA CAAAAGAAGA GGCAGCTGGA GGAATCTGTT   1740
GATTCCCTTG GTGAGGAGCT AGTCCAACTC CGAGCACAAG AGAAAGTCCA TGAAATGGAA   1800
AAAGAGCACT TGAACAAGGT TCAGACTGCA AATGAAGTCA AGCAAGCTGT TGAGCAGCAG   1860
ATCCAGAGTC ACAGAGAAAC CCACCAAAAA CAAATCAGTA GCTTGCCAGA TGAAGTTGAG   1920
GCAAAGGAAA AGCTAATCAC TGACCTCCAA GACCAAAACC AGAAGATGGT GTTGGAGCAG   1980
GAACGGCTAA GGGTGGAGCA TGAGAGGCTG AAGGCTACAG ACCAAGAGAA GAGCAGGAAG   2040
CTGCATGAGC TCACGGTTAT GCAAGACAGA CGAGAACAAG CAAGACAAGA CTTGAAGGGT   2100
TTGGAGGAGA CCGTGGCAAA AGAACTTCAG ACTTTACACA ACCTGCGTAA GCTCTTTGTT   2160
CAGGACTTGG CTACCAGGGT GAAAAGAGG CCGAGGTCGA CTCTGACGAC ACTGGCGGCA   2200
GTGCTGCACA GAAGCAGAAA ATCTCCTTCC TTGAAAACAA CCTTGAACAG CTCACCAAAG   2280
TGCACAAGCA GTTGGTACGT GATAATGCAG ATCTTCGCTG TGAGCTTCCT AAGTTAGAGA   2340
AACGGCTTAG AGCTACTGCA GAAAGAGTGA AAGCTTTGGA GTCAGCCCG              2389
```

Hind III-ATG adaptor:

5'-CTCCCAAGCTTATGGATGGATG-3'
3'-AAAGAGGGTTCGAATACCTACCTAC-5'

Cla I-stop adaptor:

5'-TGAGTGAGTGAATCGATGATTAAA-3'
3'-ACTCACTCACTTAGCTACTAA-5'

Figure 9B

Adriamycin
[μg/mL]

Camptothecin [μg/mL]

Colchicine
[μg/mL]

Act D
[μg/mL]

control        anti-KHCS GSE

ASSOCIATION OF KINESIN WITH SENSITIVITY TO CHEMOTHERAPEUTIC DRUGS

This application is a divisional application of U.S. Ser. No. 09/235,546, filed Jan. 22, 1999, now U.S. Pat. No. 6,043,340, issued Mar. 28, 2000, which is a divisional application of U.S. Ser. No. 08/486,382, filed Jun. 7, 1995, now U.S. Pat. No. 5,866,327, issued Feb. 2, 1999, which is a continuation of U.S. Ser. No. 8/177,571, filed Jan. 5, 1994, now abandoned, which is a continuation-in-part of U.S. patent application Ser. No. 08/033,086, filed Mar. 3, 1993, which in turn is a continuation-in-part of U.S. patent application Ser. No. 08/039,385, corresponding to International Patent Application Ser. No. PCT/US91/07492, filed on Oct. 11, 1991 and which entered the National stage in the U.S. on Apr. 15, 1993, which is a continuation-in-part of U.S. Ser. No. 07/599,730, filed Oct. 19, 1990, now U.S. Pat. No. 5,217,889, issued Jun. 8, 1993.

This invention was made with government support under grants CA-56736-02 by the National Institutes of Health. The government has certain rights in the invention.

BACKGROUND OF THE INVENTION

1. Field of the Invention

The invention relates to genetic factors associated with sensitivity to chemotherapeutic drugs. More particularly, the invention relates to methods for identifying such factors as well as to uses for such factors. The invention specifically provides genetic suppressor elements derived from mammalian kinesin genes, and therapeutic and diagnostic uses related thereto.

2. Summary of the Related Art

A broad variety of chemotherapeutic agents are used in the treatment of human cancer. For example the textbook *CANCER: Principles & Practice of Oncology*, 2d Edition, (De Vita et al., eds.), J.B. Lippincott Company, Philadelphia, Pa. (1985) discloses as major antineoplastic agents the plant alkaloids vincristine, vinblastine, and vindesine; the antibiotics actinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, bis-diaminedichloro-platinum, azetidinylbenzoquinone; and the miscellaneous agents dacarbazine, mAMSA and mitoxantrone.

These and other chemotherapeutic agents such as etoposide and amsacrine have proven to be very useful in the treatment of cancer. Unfortunately, some tumor cells become resistant to specific chemotherapeutic agents, in some instances even to multiple chemotherapeutic agents. Such drug resistance or multiple drug resistance can theoretically arise from either the presence of genetic factors that confer resistance to the drugs, or from the absence of genetic factors that confer sensitivity to the drugs. The former type of factors have been identified, and include the multiple drug resistance gene mdr-1 (see Chen et al., Cell 47: 381–389). However, the latter type of factor remains largely unknown, perhaps in part because the absence of such factors would tend to be a recessive trait.

Identification of genes associated with sensitivity to chemotherapeutic agents is desirable, because the discovery of such genes can lead to both diagnostic and therapeutic approaches for cancer cells and for drug resistant cancer cells, as well as to improvements in gene therapy and rational drug design. Recently, some developments have been made in the difficult area of isolating recessive genetic elements, including those involved in cytotoxic drug sensitivity. Roninson et al., U.S. Pat. No. 5,217,889 (issued Jun. 8, 1993) teach a generalized method for obtaining genetic suppressor elements (GSEs), which are dominant negative factors that confer the recessive-type phenotype for the gene to which the particular GSE corresponds. (See also Holzmayer et al., 1992, Nucleic Acids Res. 20: 711–717). Gudkov et al., 1993, Proc. Natl. Acad. Sci. USA 90: 3231–3235 teach isolation of GSEs from topoisomerase II cDNA that induce resistance to topoisomerase II-interactive drugs. Co-pending U.S. patent application Ser. No. 08/033,986, filed Mar. 3, 1993, discloses the discovery by the present inventors of a novel and unexpected result of experiments performed to identify GSEs isolated from RNA of cells resistant to the anticancer DNA damaging agent, etoposide. This reference discloses that a GSE encoding an antisense RNA homologous to a portion of a mouse kinesin heavy chain gene has the capacity to confer etoposide resistance to cells expressing the GSE. The experiments described in this reference also demonstrate that under-expression of the particular kinesin heavy chain gene disclosed therein was associated with naturally-occurring etoposide resistance in cultures of drug-selected human adenocarcinoma cells. These results were particularly unexpected because the role of kinesin genes in etoposide resistance was unknown in the art prior to the instant inventors' discoveries.

The kinesins comprise a family of motor proteins involved in intracellular movement of vesicles or macromolecules along microtubules in eukaryotic cells (see Vale, 1987, Ann. Rev. Cell Biol. 3: 347–378; and Endow, 1991, Trends Biochem. Sci. 16: 221–225 for reviews). Among the family of kinesin genes are encoded kinesin light chains and kinesin heavy chains that assemble to form mature kinesin. A number of kinesin genes have been isolated in the prior art.

Gauger and Goldstein, 1993, J. Biol. Chem. 268: 13657–13666 disclose cloning and sequencing of a Drosophila kinesin light chain gene.

Navone et al., 1992, J. Cell. Biol. 117: 1263–1275 disclose cloning and sequencing of a human kinesin heavy chain gene.

Kato, 1991, J. Neurosci. 2: 704–711 disclose cloning and sequencing of a mouse kinesin heavy chain gene.

Cyr et al., 1991, Proc. Natl. Acad. Sci. USA 88: 10114–10118 disclose cloning and sequencing of a rat kinesin light chain gene.

McDonald & Goldstein, 1990, Cell 61: 991–1000 disclose isolation of a Drosophila kinesin heavy chain gene.

Kosik et al., 1990, J. Biol. Chem. 265: 3278–3283 disclose isolation of a squid kinesin heavy chain gene.

The present inventors have demonstrated that a heretofore unexpected gene, a kinesin heavy chain gene, is involved in cellular sensitivity to the anticancer drug etoposide, and that down-regulation of functional expression of this kinesin heavy chain gene is associated with resistance to this drug. Further experiments, disclosed herein, have suggested that the role of kinesin genes in chemotherapeutic drug resistance may not be limited to this single member of the kinesin gene family. These results further underscore the power of the GSE technology developed by these inventors to elucidate unexpected mechanisms of drug resistance in cancer cells, thereby providing the opportunity and the means for overcoming drug resistance in cancer patients. Reagents and methods directed towards such goals are provided in this disclosure.

BRIEF SUMMARY OF THE INVENTION

The invention provides genetic suppressor elements (GSEs) that are random fragments derived from genes associated with sensitivity to chemotherapeutic drugs, and that confer resistance to chemotherapeutic drugs and DNA damaging agents upon cells expressing such GSEs. The invention specifically provides GSEs derived from cDNA and genomic DNA encoding kinesin genes. Diagnostic assays useful in determining appropriate candidate cancer patients bearing tumors likely to be successfully reduced or eliminated by administration of particular anticancer treatment modalities, including chemotherapeutic drugs and other DNA damaging agents, are provided by the invention, on the basis of levels of kinesin gene expression in the tumor cells borne by such cancer patients. In vitro drug screening and rational drug design methods are also within the scope of the instant disclosure.

The invention is based in part on the discoveries disclosed in co-pending U.S. patent application Ser. No. 08/033,086, filed Mar. 3, 1993 and incorporated by reference, providing a method for identifying and isolating GSEs that confer resistance to any chemotherapeutic drug for which resistance is possible. Particularly provided herein are methods for identifying GSEs derived from any kinesin gene, said GSEs being capable of conferring resistance to DNA damaging agents on cells expressing the GSEs. This method utilizes chemotherapeutic drug selection of cells that harbor clones from a random fragment expression library derived from kinesin-specific cDNA, and subsequent rescue of library inserts from drug-resistant cells. In a second aspect, the invention provides GSEs comprising oligonucleotides and/or peptides derived from kinesin genes that function as GSEs in vivo and confer on cells expressing said GSEs resistance to DNA damaging agents, including certain chemotherapeutic drugs. In a third aspect, the invention provides a method for obtaining GSEs having optimized suppressor activity for a kinesin gene associated with sensitivity to a chemotherapeutic drug. This method utilizes chemotherapeutic drug selection of cells that harbor clones from a random fragment expression library derived from DNA of a kinesin gene associated with sensitivity to that chemotherapeutic drug, and subsequent rescue of the library inserts from drug resistant cells. Particularly and preferably provided are such optimized GSEs derived from a mouse or human kinesin gene. In a fourth aspect, the invention provides synthetic peptides and oligonucleotides that confer upon cells resistance to DNA damaging agents, including certain chemotherapeutic drugs. These synthetic peptides and oligonucleotides are designed based upon the sequence of a drug-resistance conferring GSE derived from a mouse or human kinesin gene according to the invention.

In a fifth aspect, the invention provides a diagnostic assay for tumor cells that are resistant to one or more therapeutic DNA damaging agents and, at the same time, sensitive to therapeutic anti-microtubular agents, due to the absence of expression or under-expression of a kinesin gene. This diagnostic assay comprises quantitating the level of expression of any particular kinesin gene product in a particular tumor cell sample to be tested, and comparing the expression levels so obtained with a standardized set of cell lines expressing varying amounts of kinesin gene mRNA and/or protein and having different degrees of resistance to chemotherapeutic drugs and DNA damaging agents associated with their levels of kinesin gene expression. In preferred embodiments, such a standardized set of cell lines is matched by tissue type with the tissue type of the tumor cells to be evaluated.

In a sixth aspect, the invention provides methods for determining the appropriateness of candidates for particular cancer chemotherapeutic treatment modalities. In one preferred embodiment, the invention provides a means for determining whether a cancer patient is an appropriate candidate for treatment with DNA damaging chemotherapeutic drugs or other DNA damaging agents such as radiation, the method determining whether a kinesin gene, such as the kinesin heavy chain gene disclosed herein and in co-pending U.S. patent application Ser. No. 08/033,086, is over-expressed or under-expressed in tumor cells borne by a cancer patient, relative to a standardized set of cell lines as disclosed herein. Using this method, appropriate candidates for treatment with DNA damaging agents, including certain chemotherapeutic drugs, will be those patients whose tumor cells over-express the kinesin gene. In another embodiment, the invention provides a means for determining whether a cancer patient is an appropriate candidate for treatment with anti-microtubular chemotherapeutic drugs. Using this aspect of the method, appropriate candidates for anti-microtubular agent treatment will be those patients whose tumor cells under-express the kinesin gene compared with expression levels in a standardized set of cell lines. In a particularly useful embodiment of this aspect of the invention, potential candidate cancer patients for treatment with anti-microtubular anticancer agents will have failed or proven resistant to a course of cancer chemotherapy using DNA damaging agents.

In a seventh aspect, the invention provides a starting point for the rational design of pharmaceutical products that are useful against tumor cells that are resistant to chemotherapeutic drugs. By examining the structure, function, localization and pattern of expression of kinesin genes associated with resistance to DNA damaging agents and sensitivity to anti-microtubular chemotherapeutic drugs, strategies can be developed for creating pharmaceutical products that will overcome drug resistance in tumor cells in which such kinesin genes are either over-expressed or under-expressed.

Specific preferred embodiments of the present invention will become evident from the following more detailed description of certain preferred embodiments and the claims.

BRIEF DESCRIPTION OF THE DRAWINGS

FIG. 1 shows the overall construction scheme. FIG. 2B shows normalization of the cDNA fragments. In this panel, t represents total unfractionated cDNA, s and d represent the single-stranded and double-stranded fractions separated by hydroxyapatite, time points indicate the period of reannealing, and tubulin, c-myc, and c-fos indicate the probes used in Southern hybridization with the total, single-stranded and double-stranded fractions.

FIG. 6 shows the nucleotide sequence of the GSE anti-khcs (SEQ.ID.No.:3.)

FIGS. 7A through 7C shows the nucleotide sequence of most of the coding region of the mouse khcs cDNA (SEQ.ID.No.:4).

FIGS. 9A and 9B illustrates the experimental protocol for drug-selected production of kinesin-derived GSEs (FIG. 9A) and the structure of the adaptors used for the preparation of a random fragment KHCS cDNA library (FIG. 9B).

DETAILED DESCRIPTION OF THE PREFERRED EMBODIMENTS

Figure 1A:
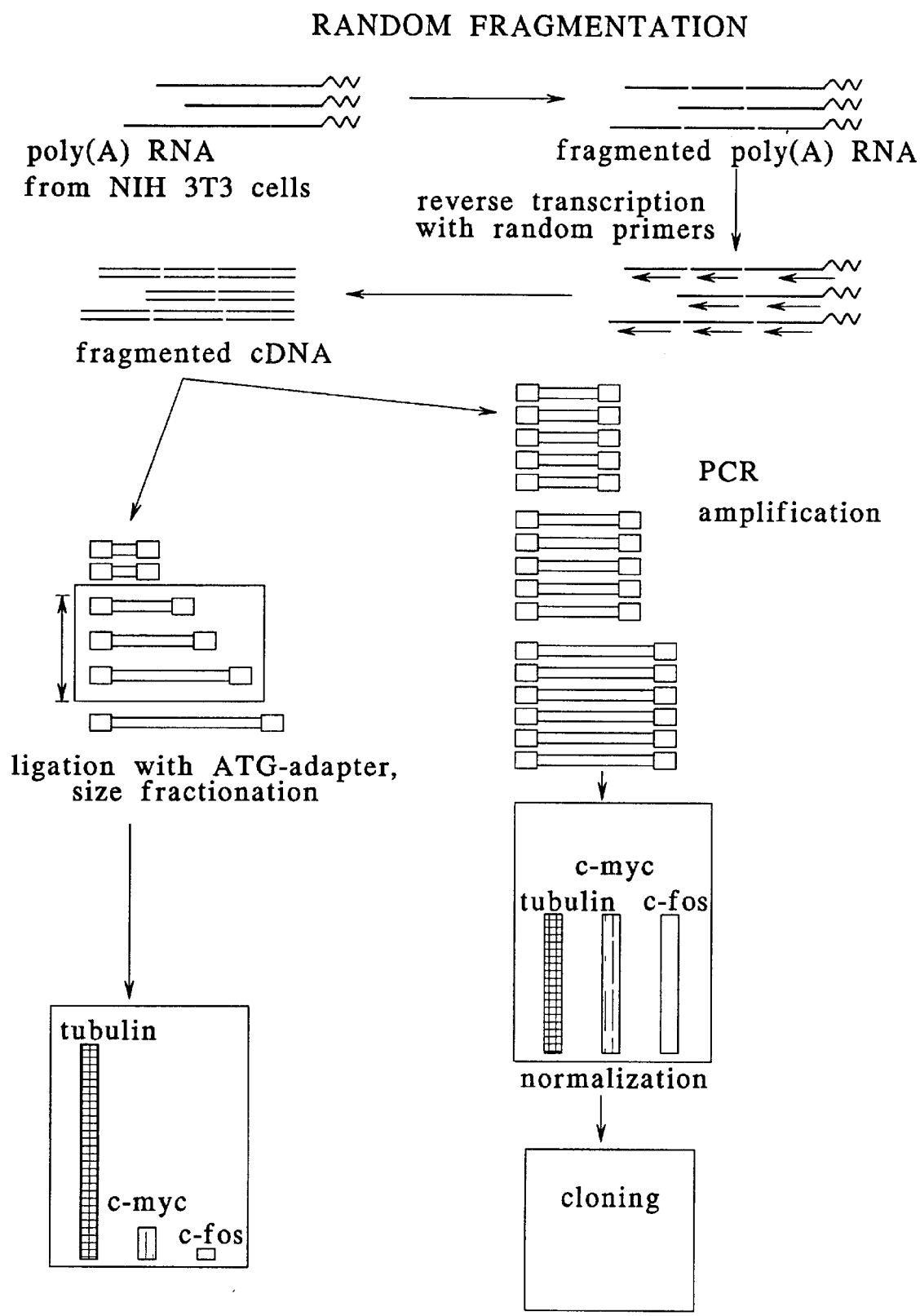
FIGS. 1 and 2B shows a scheme for construction of a random fragment expression library (RFEL) from NIH 3T3 cDNA.

The invention relates to means for suppressing specific gene functions that are associated with sensitivity and resistance to chemotherapeutic drugs. The invention provides genetic suppressor elements (GSEs) derived from kinesin genes that have such suppressive effect and thus confer resistance to DNA damaging agents including chemotherapeutic drugs. The invention further provides methods for identifying such GSEs, as well as methods for their use.

For the purposes of this invention, the term "kinesin gene" will be understood to encompass any kinesin gene, particularly mammalian, and preferably mouse or human, kinesin genes. Kinesins comprise a family of related genes encoding a number of related motor proteins involved in intracellular movement of vesicles or macromolecules along microtubules in eukaryotic cells (see Background of the Invention). The mature, functional kinesin molecule is comprised of products of a kinesin heavy chain gene and a kinesin light chain gene. The instant invention encompasses GSEs derived from both kinesin light chain and kinesin heavy chain genes. The invention specifically is intended to contain within its scope all kinesin genes and GSEs derived therefrom that are capable of causing resistance or sensitivity to DNA damaging agents.

The DNA damaging agents that fall within the scope of this invention are all DNA damaging agents, including but not limited to ionizing and ultraviolet radiation, and certain chemotherapeutic drugs, including amsacrine, etoposide, doxorubicin (Adriamycin), cisplatin, and camptothecin.

In a first aspect, the invention provides a GSE derived from the cDNA of a mouse kinesin heavy chain gene isolated from a normalized, random fragment expression library made from total cellular mRNA from NIH 3T3 cells and isolated on the basis of its ability to confer resistance to the topoisomerase II drug, etoposide (described in Examples 1–4 herein and co-pending U.S. patent application Ser. No. 08/033,086, filed Mar. 3, 1993 and incorporated by reference). Prior to the discovery by the present inventors, there was no suspicion that kinesin was in any way implicated in etoposide sensitivity. These results demonstrated the ability of the general method for identifying GSEs to provide much new and surprising information about the genetic basis for resistance to chemotherapeutic drugs.

In addition, the kinesin-derived GSE conferring resistance to etoposide caused cellular effects suggesting that kinesin may be involved in programmed cell death. The method according to this aspect of the invention therefore also provides valuable information about the genetic basis for senescence and cell death. This may have important implications for studying genes involved in development, since GSEs used to identify genes associated with chemotherapeutic drug resistance or senescence can also be expressed as transgenes in embryos to determine the role of such genes in development. The elucidation of the structure of the mouse kinesin heavy chain gene corresponding to this drug resistance-related GSE is described in Example 5 and functional analyses of the drug resistance capacity of this GSE is disclosed in Example 7.

In a second aspect, the invention provides a method for identifying kinesin gene-derived GSEs that confer resistance to a DNA damaging agent. The GSEs identified by this method will be homologous to a kinesin gene. For purposes of the invention, the term "homologous to" a kinesin gene has two different meanings, depending on whether the GSE acts through an antisense mechanism or antigene mechanism (i.e., through a mechanism of interference at the protein level). In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene; in particular, any kinesin gene, preferably any mouse or human kinesin gene, as disclosed herein.

The method according to this aspect of the invention comprises the step of screening a kinesin-specific cDNA or kinesin-specific genomic DNA random fragment expression library phenotypically to identify clones that confer resistance to a DNA damaging agent such as certain chemotherapeutic drugs. Preferably, the library of random fragments of kinesin-specific cDNA or kinesin-specific genomic DNA is cloned into a retroviral expression vector. In this preferred embodiment, retrovirus particles containing the library are used to infect cells and the infected cells are tested for their ability to survive in a concentration of a DNA damaging agent that kills uninfected cells. Preferably, the inserts in the library will range from about 100 basepairs (b.p.) to about 700 b.p. and more preferably, from about 200 b.p. to about 500 b.p. Once a clonal population of cells that are resistant to the DNA damaging agent has been isolated, the library clone encoding the GSE is rescued from the cells. At this stage, the nucleotide sequence of the insert of the expression library may be determined; in clones derived from a kinesin gene-specific cDNA random fragment expression library, the nucleotide sequence is expected to be homologous to a portion of the kinesin gene cDNA nucleotide sequence. Alternatively, the rescued library clone may be further tested for its ability to confer resistance to DNA damaging agents and chemotherapeutic drugs in additional transfection or infection and selection assays, prior to nucleotide sequence determination. Determination of the nucleotide sequence, of course, results in the identification of the GSE. This method is further illustrated in Example 6.

Thus, the invention provides a method for obtaining kinesin gene-derived GSEs having optimized suppressor activity. By screening a random fragment expression library made exclusively from kinesin gene-specific fragments, a much greater variety of GSEs derived specifically from the kinesin gene can be obtained, compared with a random fragment library prepared from total cDNA as in Example 1. Consequently, the likelihood of obtaining optimized GSEs, i.e., those kinesin-derived GSEs conferring an optimal level of resistance to a chemotherapeutic drug, is maximized using the single gene random fragment library approach, as is shown in greater detail in Example 6.

An additional feature of this aspect of the invention is the production of a multiplicity of kinesin-specific GSEs by drug selection of cells producing infectious retroviral embodiments of the kinesin-derived GSEs of the invention. In this aspect, ecotropic cells infected with a kinesin cDNA or kinesin genomic DNA-specific random fragment expression library are subjected to selection with a DNA damaging agent, preferably and most practically a chemotherapeutic drug such as etoposide. A population of resistant clones are thereby obtained, each containing a drug resistance-conferring, kinesin-derived GSE. Since these cells are capable of producing infectious retroviral embodiments of the GSEs of the invention, a multiplicity of kinesin-derived GSEs, pre-selected for the ability to confer drug resistance, can be easily and efficiently produced.

In a fourth aspect, the invention provides synthetic peptides and oligonucleotides that are capable of inhibiting the function of kinesin genes associated with sensitivity to chemotherapeutic drugs. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE has been discovered and sequenced, and its orientation is determined, it is straightforward to prepare an oligonucleotide corresponding to the nucleotide sequence of the GSE (for antisense-oriented GSEs) or amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus, but generally not both. This suggests that many GSE's have one critical endpoint, from which a simple walking experiment will determine the minimum size of peptide or oligonucleotide necessary to inhibit gene function. For peptides, functional domains as small as 6–8 amino acids have been identified for immunoglobulin binding regions. Thus, peptides or peptide mimetics having these or larger dimensions can be prepared as GSEs. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Preferably, such oligonucleotides will have from about 12 to about 100 nucleotides. As used herein, the term oligonucleotides includes modified oligonucleotides having nuclease-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridge methylene phosphonate and bridged phosphorothioate internucleotide linkages. The synthesis of oligonucleotides containing these modified linkages is well known in the art. (See, e.g., Uhlmann and Peyman, 1990, Chemical Reviews 90: 543–584; Schneider and Banner, 1990, Tetrahedron Letters 31: 335). The term oligonucleotides also includes oligonucleotides having modified bases or modified ribose or deoxyribose sugars.

In a fifth aspect, the invention provides dominant selectable markers that are useful in gene co-transfer studies. Since GSEs according to the invention confer resistance to chemotherapeutic drugs, the presence of a vector that expresses the GSE can readily be selected by growth of a vector-transfected cell in a concentration of the appropriate cytotoxic drug that would be cytotoxic in the absence of the GSE. GSEs according to the invention are particularly well suited as dominant selectable markers because their small size allows them to be easily incorporated along with a gene to be co-transferred even into viral vectors having limited packaging capacity.

In a sixth aspect, the invention provides a diagnostic assay for tumor cells that are resistant to one or more DNA damaging agents, including certain chemotherapeutic drugs, due to the absence of expression or the under-expression of a kinesin gene. In particular, the class of DNA damaging agents resistance to which involves under-expression of a kinesin gene includes but is not limited to cisplatin, etoposide and camptothecin. To determine whether absence of expression or under-expression of a kinesin gene is a naturally occurring, and thus medically significant basis for chemotherapeutic drug resistance, human tumor cells can be treated with cytotoxic quantities of an appropriate chemotherapeutic drug to select for spontaneous drug resistant mutants. These mutants can then be assessed for their level of expression of the particular gene of interest. Absence of expression or significantly reduced expression indicates a natural mechanism of chemotherapeutic drug resistance. The description of such an experiment, disclosing that under-expression of the human kinesin heavy chain gene disclosed herein is associated with naturally-occurring resistance to the chemotherapeutic drug etoposide in cultures of etoposide-resistant human adenocarcinoma (HeLa) cells, is disclosed in Example 11 herein and in co-pending U.S. patent application Ser. No. 08/033,086, filed Mar. 3, 1993 and incorporated by reference. In a preferred embodiment of this assay, a standardized set of tissue-specific cell lines, wherein the levels of drug resistance and kinesin gene expression have been quantitated and correlated with each other, are provided for tumors from each tissue type to be assayed.

Alternatively, and preferably, collections of naturally occurring treatment-responding and non-responding tumor tissue samples can be examined for expression levels of kinesin genes, and correlations established between treatment outcome, and presumably the drug-resistant mechanisms thereof, and kinesin gene expression.

Accordingly, such reduced or absent expression can be the basis for a diagnostic assay for tumor cell resistance to a DNA damaging agent or chemotherapeutic drug or drugs of interest. A first embodiment of a diagnostic assay according to this aspect of the invention utilizes an oligonucleotide or oligonucleotides that is/are homologous to the sequence of a kinesin gene. In this embodiment, RNA is extracted from a tumor sample, and RNA specific for a particular kinesin gene is quantitated by standard filter hybridization procedures, an RNase protection assay, or by quantitative cDNA-PCR (see Noonan et al., 1990, Proc. Natl. Acad. Sci. USA 87: 7160–7164). In a second embodiment of a diagnostic assay according to this aspect of the invention, antibodies are raised against a synthetic peptide having an amino acid sequence that is identical to a portion of the kinesin heavy chain or kinesin light chain protein. Antibodies specific for the human kinesin heavy chain have in fact been disclosed (see Navone et al., supra). These antibodies are then used in a conventional quantitative immunoassay (e.g., RIA or immunohistochemical assays) to determine the amount of the gene product of interest present in a sample of proteins extracted from the tumor cells to be tested, or on the surface or at locations within the tumor cells to be tested.

A particular utility for such diagnostic assays of this invention is their clinical use in making treatment decisions for the alleviation of malignant disease in humans. For example, a determination that the kinesin heavy chain gene of this invention is under-expressed in a tumor compared with the levels of expression found in normal cells comprising that tissue would suggest that a patient bearing such a tumor might be a poor candidate for therapeutic intervention using DNA damaging agents, since it would be expected that such kinesin under-expressing cells of the tumor would be resistant to such agents. Similarly, tumor cells which fortuitously over-express the kinesin heavy chain gene of the invention would be expected to be sensitive to such agents and thus to be susceptible to tumor cell killing by these agents. On the other hand, the instant disclosure provides experimental evidence that kinesin heavy chain gene under-expressors are sensitive to the cytocidal action of anti-microtubular agents, including for example colchicine, colcemide, vinblastine, vincristine and vindesine. These results suggest that patients bearing tumors whose cells under-express the kinesin heavy chain gene of the present invention may be responsive to treatment with anti-microtubular agents. The present invention thus enables intelligent and informed therapeutic intervention based on properties of an individual cancer patient's tumor resistance or sensitivity to DNA damaging agents and other chemotherapeutic treatment modalities, where treatment choices can be made prior to initiation of treatment based on mechanisms of resistance specific for DNA damaging agents and mediated by kinesin heavy chain gene over- or under-expression. Particularly useful in this aspect of the invention are kinesin-specific antibodies, such as the anti-kinesin heavy chain antibodies described in Navone, et al., supra, for detection of kinesin expression levels in tumor samples.

In a seventh aspect, the invention provides a starting point for the rational design of pharmaceutical products that can counteract resistance by tumor cells to chemotherapeutic drugs.

Understanding the biochemical function of the kinesin genes that are involved in drug sensitivity is likely to suggest pharmaceutical means to stimulate or mimic the function of such genes and thus augment the cytotoxic response to anticancer drugs. One may also be able to up-modulate gene expression at the level of transcription. This can be done by cloning the promoter region of each of the corresponding kinesin genes and analyzing the promoter sequences for the presence of cis elements known to provide the response to specific biological stimulators. Due to the structure of the kinesins in eukaryotic cells, i.e., comprised of both kinesin heavy chain and kinesin light chain proteins, coordinate up-regulation of the expression of both of the appropriate kinesin light chain and heavy chain proteins would be required for efficacious therapeutic intervention based on modulating expression of kinesin genes.

Alternatively, kinesin expression in a cancer cell can be increased by co-introduction of recombinant expression constructs encoding functional, full-length copies of a kinesin heavy chain and a kinesin light chain, whereby coordinate co-expression of such exogenous kinesins would result in increased expression of functional kinesin molecules in the cancer cells.

The protein structure deduced from the cDNA sequence can also be used for computer-assisted drug design, to develop new drugs that affect this protein in the same manner as the known anticancer drugs. The purified protein, produced in a convenient expression system, can also be used as the critical component of in vitro biochemical screen systems for new compounds with anticancer activity. Accordingly, mammalian cells that express chemotherapeutic drug resistance-conferring GSEs according to the invention are useful for screening compounds for the ability to overcome drug resistance. As with pharmaceutical intervention methods, both kinesin light chains and heavy chains should be present in such in vitro screening systems in amounts capable of reconstituting mature kinesin molecules in vitro.

Specific preferred embodiments of the present invention will become evident from the following more detailed description of certain preferred embodiments and the claims.

EXAMPLE 1

Generation of a Normalized Random Fragment cDNA Library in a Retroviral Vector

A normalized cDNA population was prepared using a modification of the protocol of Patanjali et al. (1991, Proc. Natl. Acad. Sci. USA 88: 1943–1947), illustrated in FIG. 1. Poly(A)$^+$ RNA was extracted from NIH 3T3 cells. To obtain mRNAs for different genes expressed at various stages of the cell growth, one half of the RNA was isolated from a rapidly growing culture and the other half from quiescent cells that had reached complete monolayer confluence. To avoid over-representation of the 5'-end sequences in a randomly primed cDNA population, RNA was fragmented by boiling to an average size range of 600–1,000 nucleotides. These RNA fragments were then used for preparing randomly primed double-stranded cDNA. This randomly primed cDNA was then ligated to a synthetic adaptor providing ATG codons in all three possible reading frames and in a proper context for translation initiation. The structure of the adaptor (see FIG. 2) determined its ligation to the blunt-ended fragments of the cDNA in such a way that each fragment started from initiation codons independently from its orientation. The adaptor was not supplied with termination codons in the opposite strand since the cloning vector pLNCX, contained such codons immediately downstream of the cloning site. (This vector has been described by Miller and Rosman, 1989, Biotechniques 7: 980–986.) The ligated mixture was amplified by PCR, using the "sense" strand of the adaptor as a PCR primer, (in contrast to the method of Patanjali et al., which utilized cloning the initial cDNA preparation into a phage vector and then using vector-derived sequences as PCR primers to amplify the cDNA population.) The PCRs were carried out in 12 separate reactions that were subsequently combined, to minimize random over- or under-amplification of specific sequences and to increase the yield of the product. The PCR-amplified mixtures was size-fractionated by gel electrophoresis, and 200–500 bp fragments were selected for subsequent manipulations, (in contrast to Patanjali's fragment size range of from 400 to 1,600 bp.)

For normalization, the cDNA preparation was denatured and reannealed, using different time points for reannealing, as described by Patanjali et al., supra, and shown in FIG. 1. The single-stranded and double-stranded DNAs from each reannealed mixture were separated by hydroxyapatite chromatography. The single-stranded DNA fractions from each time point of reannealing were PCR-amplified using the adaptor-derived primer and analyzed by Southern hybridization for the relative abundance of different mRNA sequences. The fraction that contained similar proportions of tubulin, c-myc and c-fos cDNA sequences (see FIG. 2B), corresponding to high-, medium- and low-expressed genes, respectively, was used for the library preparation.

Figure 2:
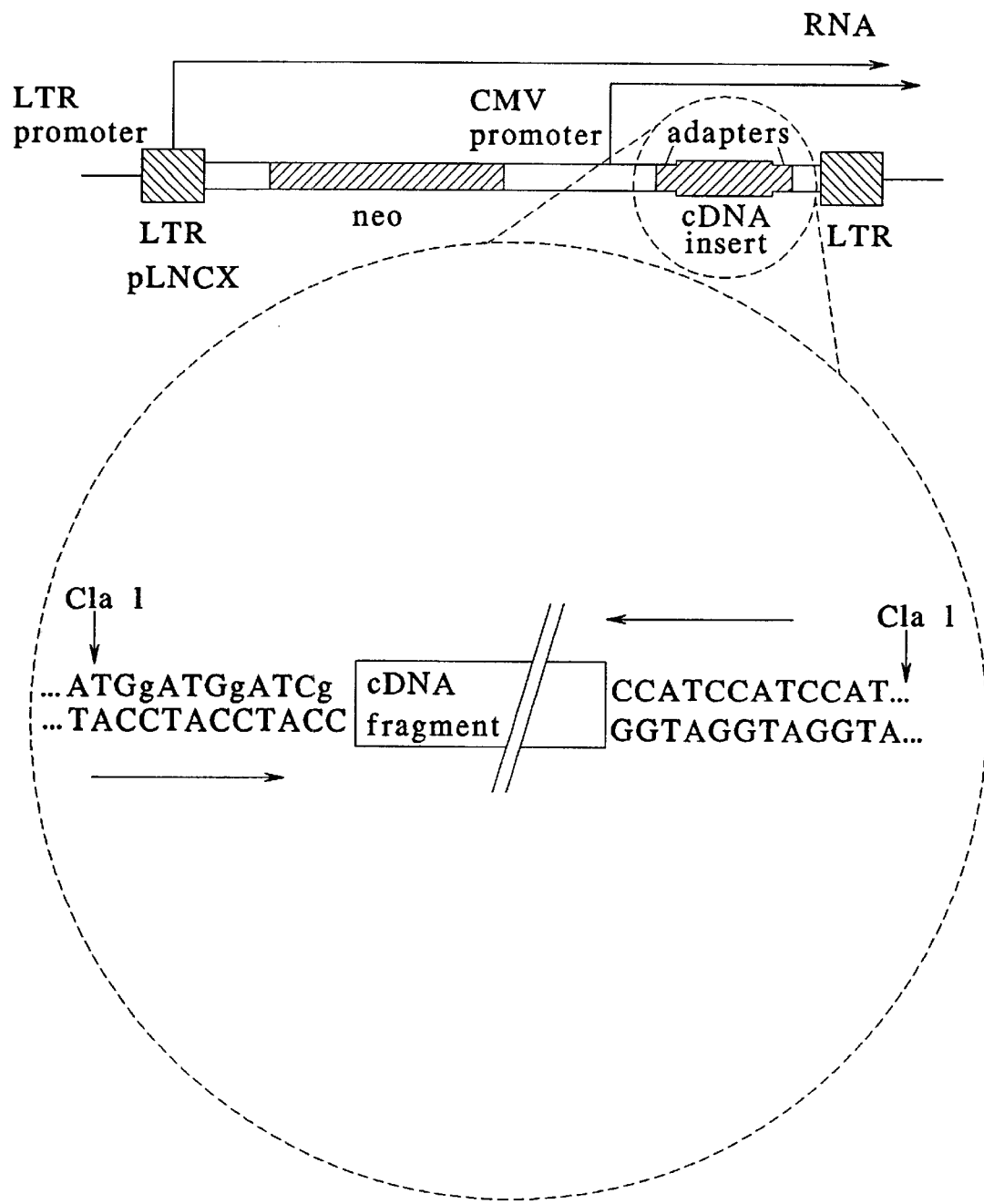
FIG. 2 shows the structure of the LNCX vector and the adaptor used in cDNA cloning. The nucleotide sequences are shown for the ATG-sense (SEQ.ID.No.:1) and ATG-antisense (SEQ.ID.No.:2) strands of the adaptor.
Figure 2B:
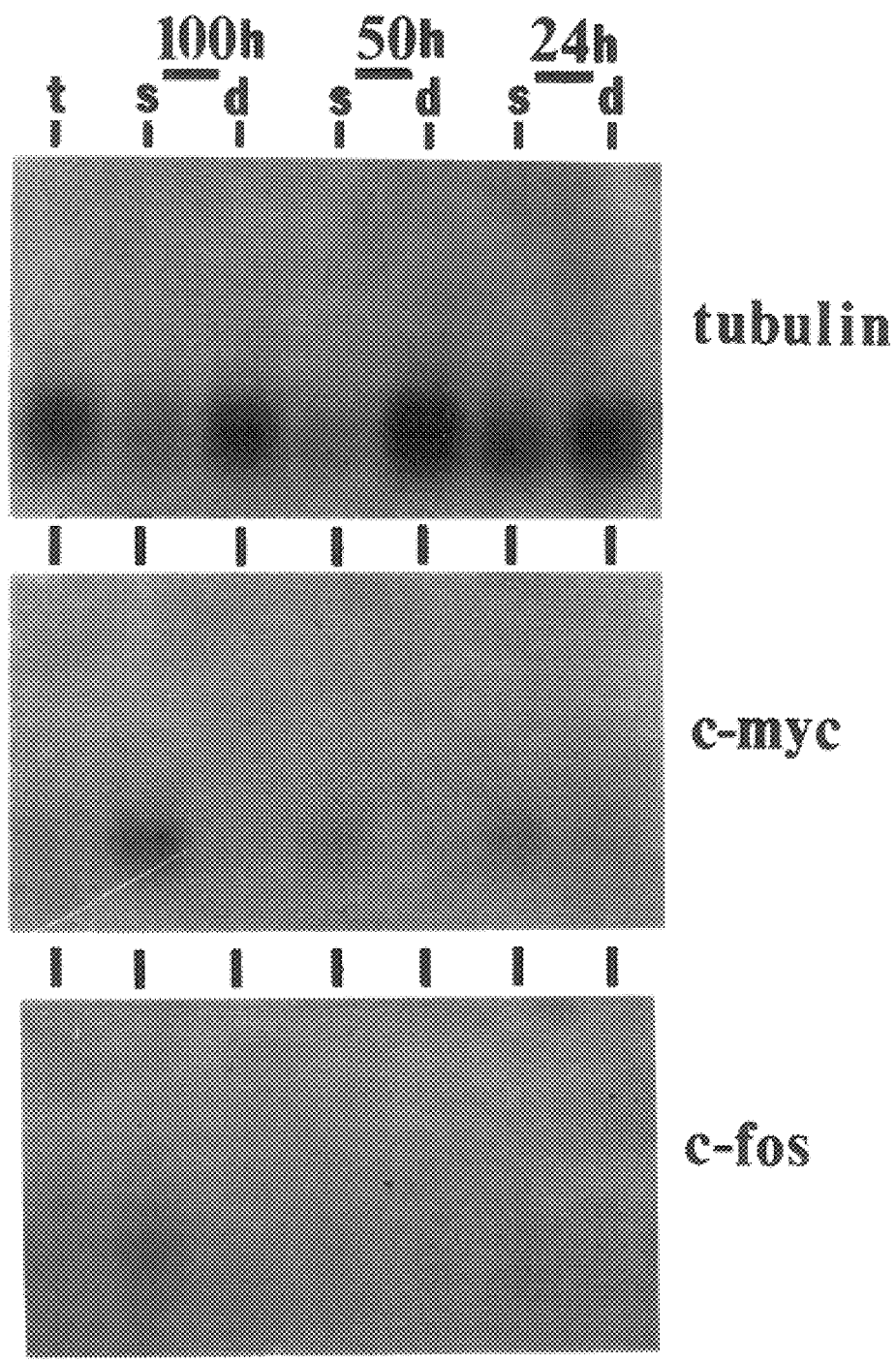

The normalized cDNA preparation was cloned into a ClaI site of the MoMLV-based retroviral vector pLNCX, which carries the neo (G418 resistance) gene, transcribed from the promoter contained in the retroviral long terminal repeat (LTR), and which expresses the inserted sequence from a strong promoter of the cytomegalovirus (CMV) (see FIG. 2). The ligation mixture, divided into five portions, was used for five subsequent large-scale transformations of E. coli. The transformed bacteria were plated on the total of 500 agar plates (150 mm in diameter) and the plasmid population (18 mg total) was isolated from the colonies washed off the agar. A total of approximately $5 \times 10^7$ clones were obtained, more than 60% of which carried the inserts of normalized cDNA, as estimated by PCR amplification of inserts from 50 randomly picked colonies. These results demonstrate the feasibility of generating a normalized cDNA library of as many as $3 \times 10^7$ recombinant clones in a retroviral plasmid expression vector.

EXAMPLE 2

Transduction of a Retroviral Random Fragment Library into Virus-Packaging Cell Lines and NIH 3T3 Cells The plasmid library prepared according to Example 1 was converted into a mixture of retroviral particles by transfection into virus-packaging cells (derivatives of NIH 3T3) that express retroviral virion proteins. (Examples of such cell lines have been described by Markowitz et al., 1988, Virology 167: 400–406.) Ecotropic and amphotropic virus-packaging cell lines, GP+E86 and GP+envAm12, respectively, were mixed at a 1:1 ratio and $10^7$ cells of this mixture were transfected with the plasmid library under standard calcium phosphate coprecipitation conditions. This transfection resulted in the packaging and secretion of ecotropic and amphotropic virus particles, which rapidly spread through the packaging cell population, since ecotropic viruses are capable of infecting amphotropic packaging cells and vice versa. The yield of the virus, as measured by the number of G418-resistant colonies obtained after the infection of NIH 3T3 cells, reached $10^5$ infectious units per 1 mL of media during the stage of transient transfection (1–3 days), then decreased (4–8 days) and then rapidly increased due to the expression of proviral genomes that became stably integrated in most of the packaging cells. The yield of the virus 9–12 days after transfection reached >$10^6$ per 1 mL of media supernatant. At this stage, the library showed fairly even representation of different fragments, but at later stages individual virus-producing clones began to predominate in the population, leading to uneven representation of cDNA-derived inserts. The uniformity of sequence representation in the retroviral population was monitored by rapid extraction of DNA from cells infected with the virus-containing supernatant, followed by PCR amplification of inserts. The inserts were analyzed first by the production of a continuous smear in ethidium bromide-stained agarose gel and then by Southern hybridization with different probes, including topoisomerase II, c-myc and tubulin. As long as each gene was represented by a smear of multiple fragments, the representativity of the library was considered to be satisfactory.

In other experiments, for transducing the random-fragment normalized cDNA library into NIH 3T3 cells, without loss of representativity, NIH 3T3 cells were infected either with a virus produced at the transient stage of transfection (days 1–3), or with the high-titer virus collected 10–12 days after transfection. In the latter case, 100 ml of viral suspension contained more than $10^8$ infectious units. In the case of the "transient" virus, NIH 3T3 cells were infected with at least $10^7$ recombinant retroviruses by using 500 ml of media from virus-producing cells (five rounds of infection, 100 ml of media in each). These results demonstrate the feasibility of converting a large and complex random fragment library into retroviral form and delivering it to a non-packaging cell line without loss of complexity.

EXAMPLE 3

Isolation of GSEs Conferring Resistance to the Chemotherapeutic Drug Etoposide

Figure 3:
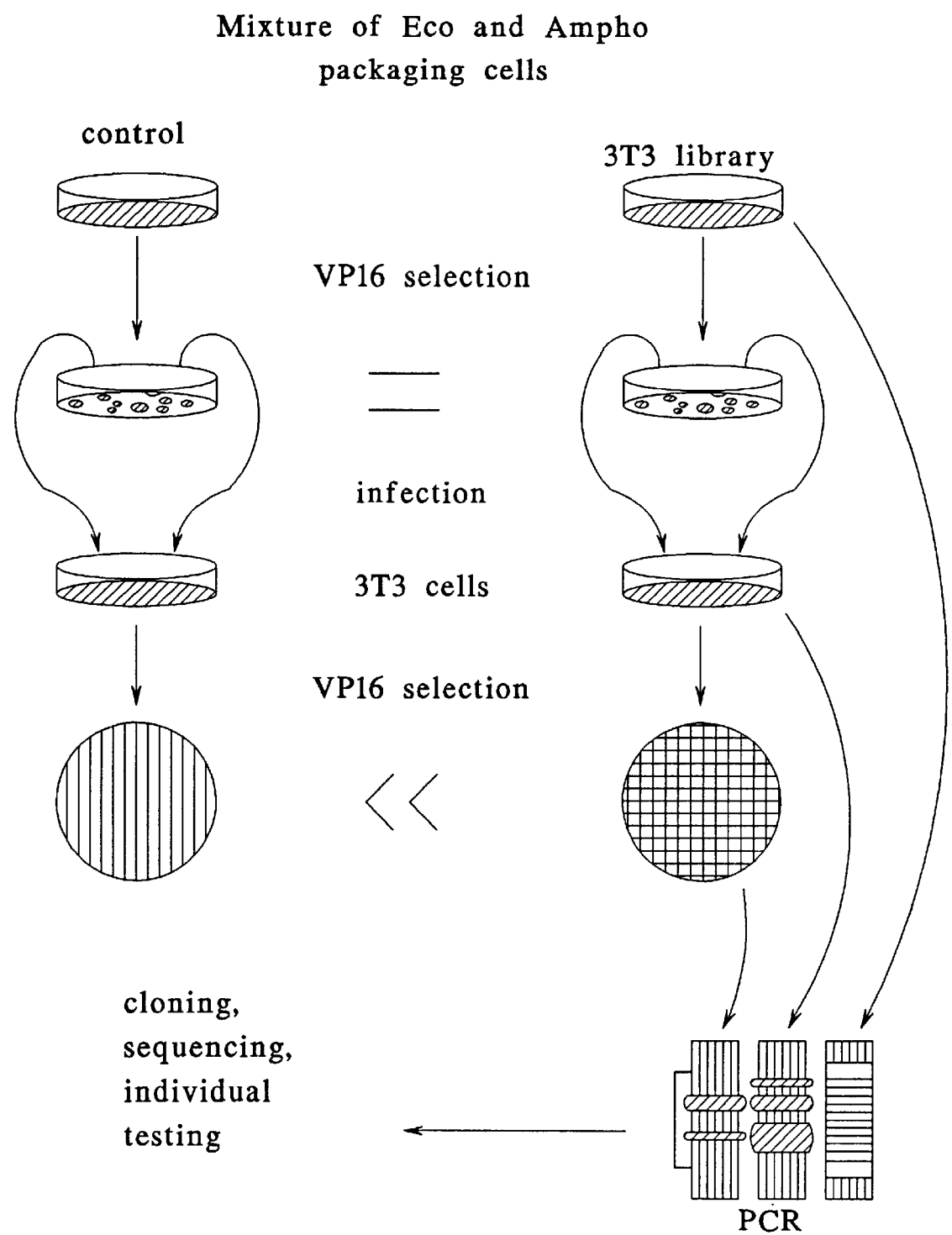
FIG. 3 shows the overall scheme for selecting cell lines containing chemotherapeutic drug resistance-conferring GSEs and rescuing the GSEs from these cells.
Figure 4A:
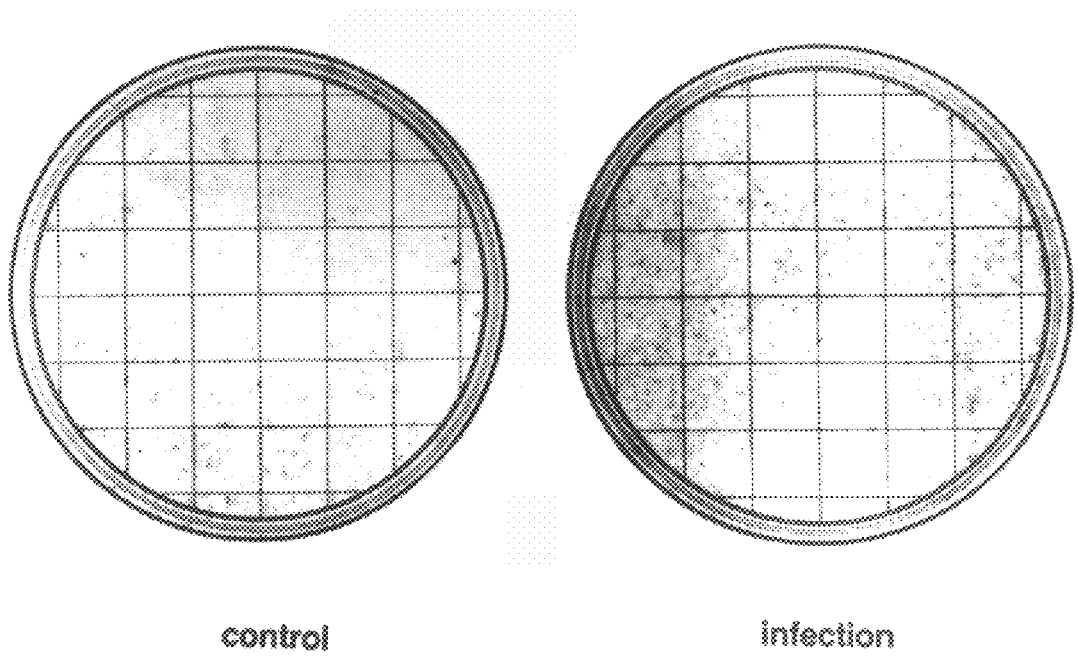
FIG. 4A shows etoposide resistance conferred by preselected virus.

The overall scheme for the selection of GSEs conferring etoposide resistance is illustrated in FIG. 3. This selection was carried out directly on virus-producing packaging cells, in the expectation that cells whose resistant phenotype is caused by the GSE expression will produce virus particles carrying such a GSE. The mixture of amphotropic and ecotropic packaging cells was transfected with the cDNA library in the LNCX vector, prepared according to Example 1, and the virus was allowed to spread through the population for 9 days. Analysis of a small part of the population for G418 resistance showed that practically 100% of the cells carried the neo-containing provirus. The cells were then exposed to 350 ng/mL etoposide for 15 days and then allowed to grow without drug for two more weeks. No difference was observed between the numbers of colonies obtained in the experiment and in the control (uninfected cells or cells infected with the insert-free LNCX virus) after etoposide selection. The virus present in the media supernatant of the surviving cells was then used to infect NIH 3T3 cells followed by etoposide selection using essentially the same protocol. NIH 3T3 cells infected with the library-derived virus produced by packaging cells that were selected with etoposide showed a major increase in the number of etoposide-resistant cells relative to the control cells infected with the insert-free LNCX virus, indicating the presence of biologically active GSEs in the preselected virus population (see FIG. 4A).

Figure 4B:
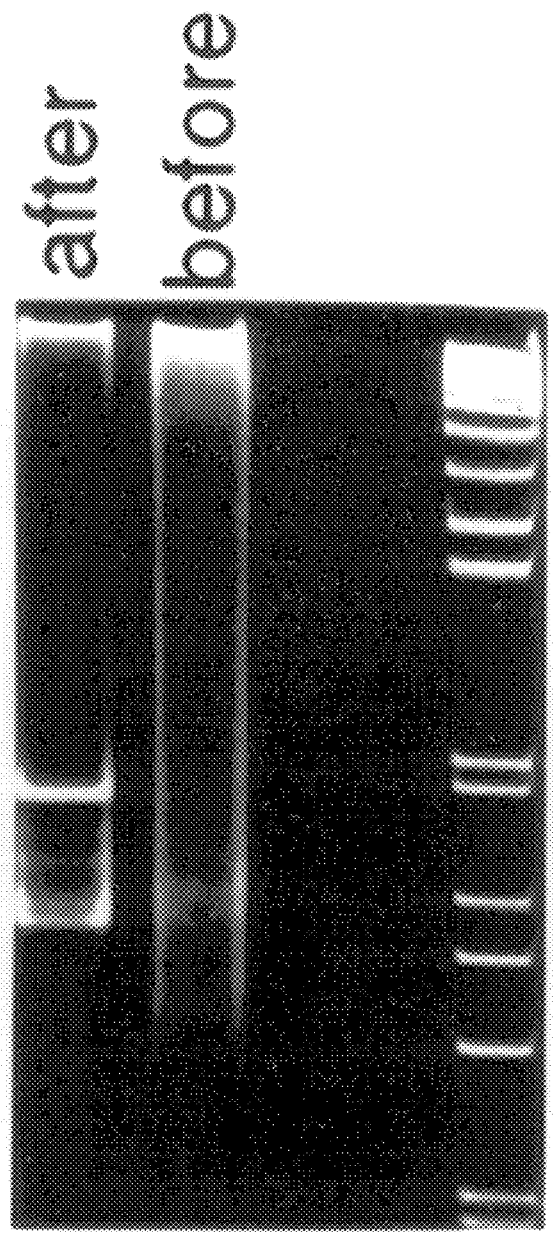
FIG. 4B shows PCR analysis of the selected and unselected population.
Figure 4C:
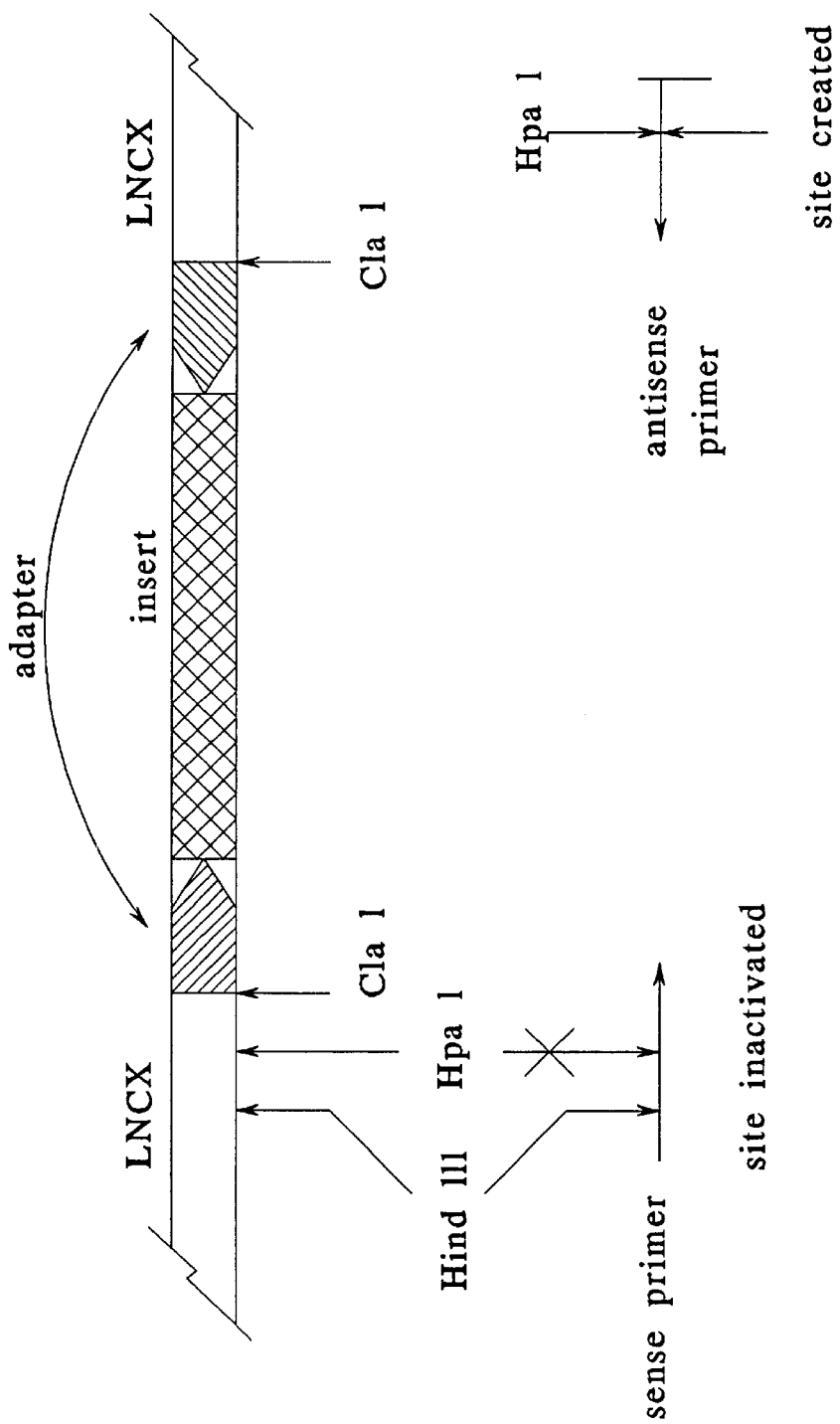
FIG. 4C depicts the scheme for the GSE recloning experiment described in Example 3.
Figure 5A:
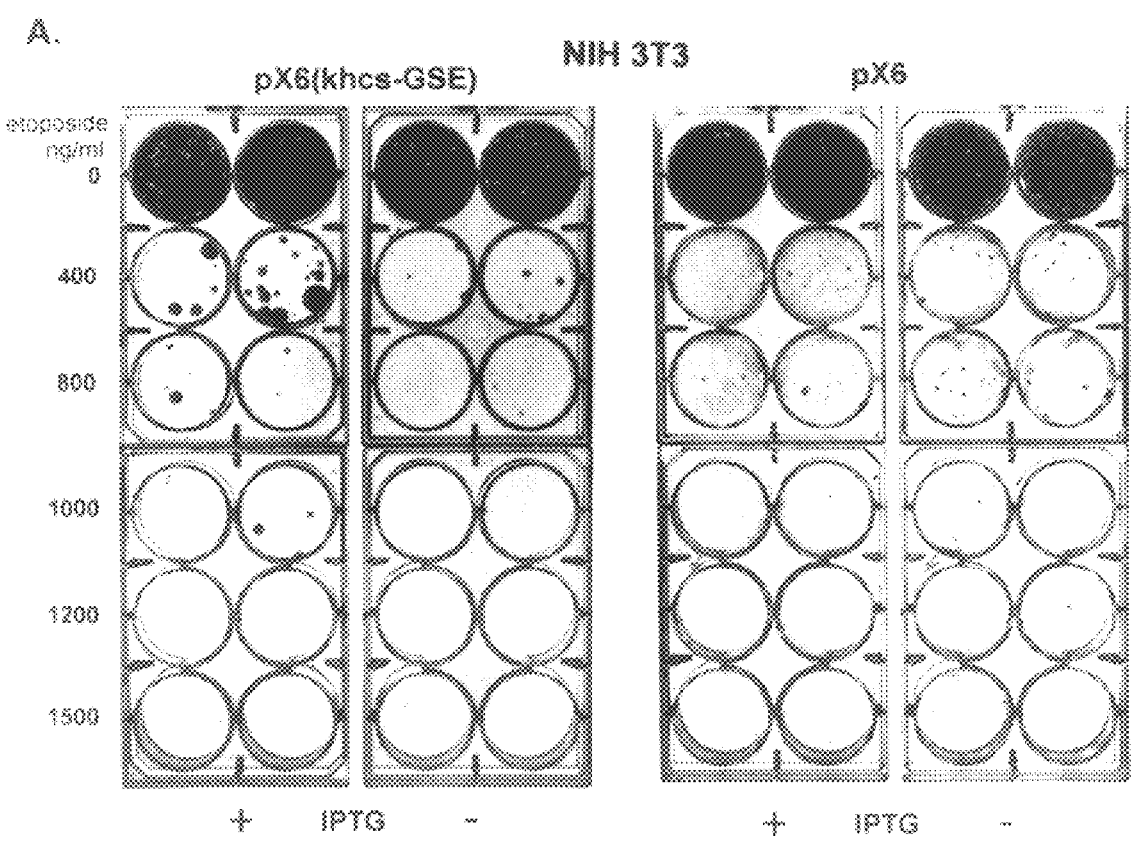
FIGS. 5A and 5B shows resistance to various concentrations of etoposide, conferred upon the cells by the GSE anti-khcs under an IPTG-inducible promoter (FIG. 5A), the scheme for this experiment (FIG. 5B).

The proviral inserts contained in the etoposide-selected NIH 3T3 cells were analyzed by PCR. This analysis (see FIG. 4B) showed an enrichment for specific fragments, relative to the unselected population of the infected cells. Individual PCR-amplified fragments were recloned into the LNCX vector in the same position and orientation as in the original plasmid, as illustrated in FIG. 4C. A total of 42 proviral inserts, enriched after etoposide selection, were thus recloned, and tested either in batches or individually for the ability to confer increased etoposide resistance after retroviral transduction into NIH 3T3 cells. Three non-identical clones were found to induce etoposide resistance, indicating that they contained biologically active GSEs. These GSEs wee named anti-khcs, VPA and VP9–11. Etoposide resistance induced by the clone named anti-khcs is illustrated in FIG. 5A.

Figure 5B:
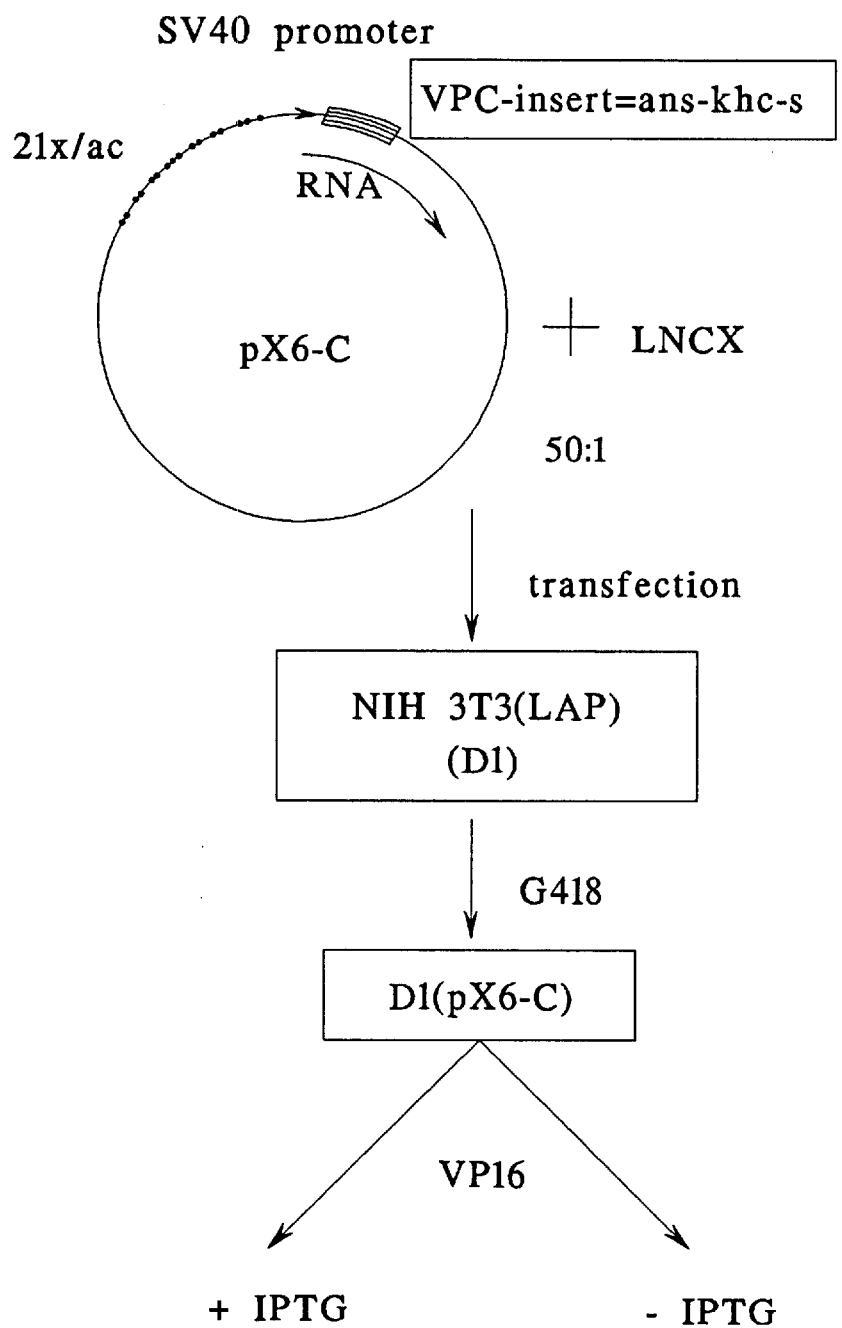
Figure 8A:
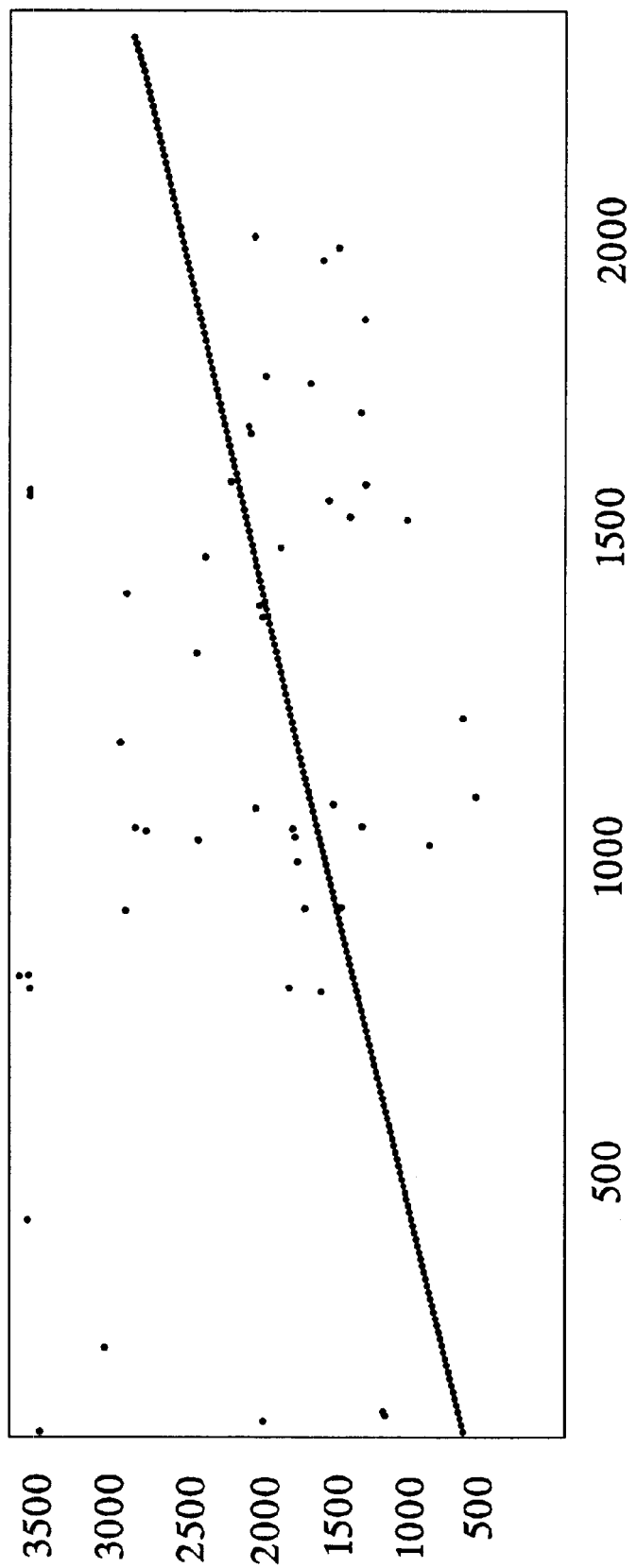
FIGS. 8A through 8D shows the dot matrix alignments of khcs protein sequence deduced from the nucleotide sequence in FIGS. 7A through 7C with kinesin heavy chain sequences from human (FIG. 8A), mouse (FIG. 8B), fruit fly (FIG. 8C), and squid (FIG. 8D).
Figure 8B:
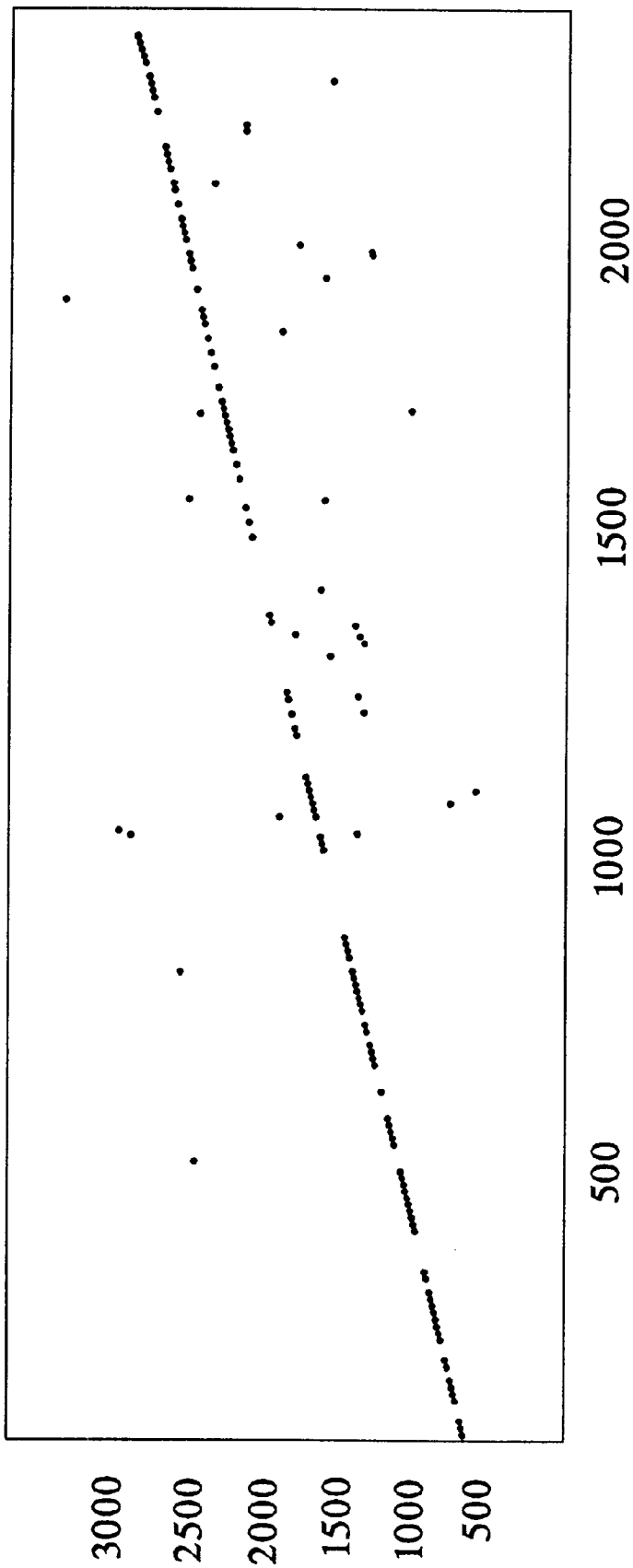
Figure 8C:
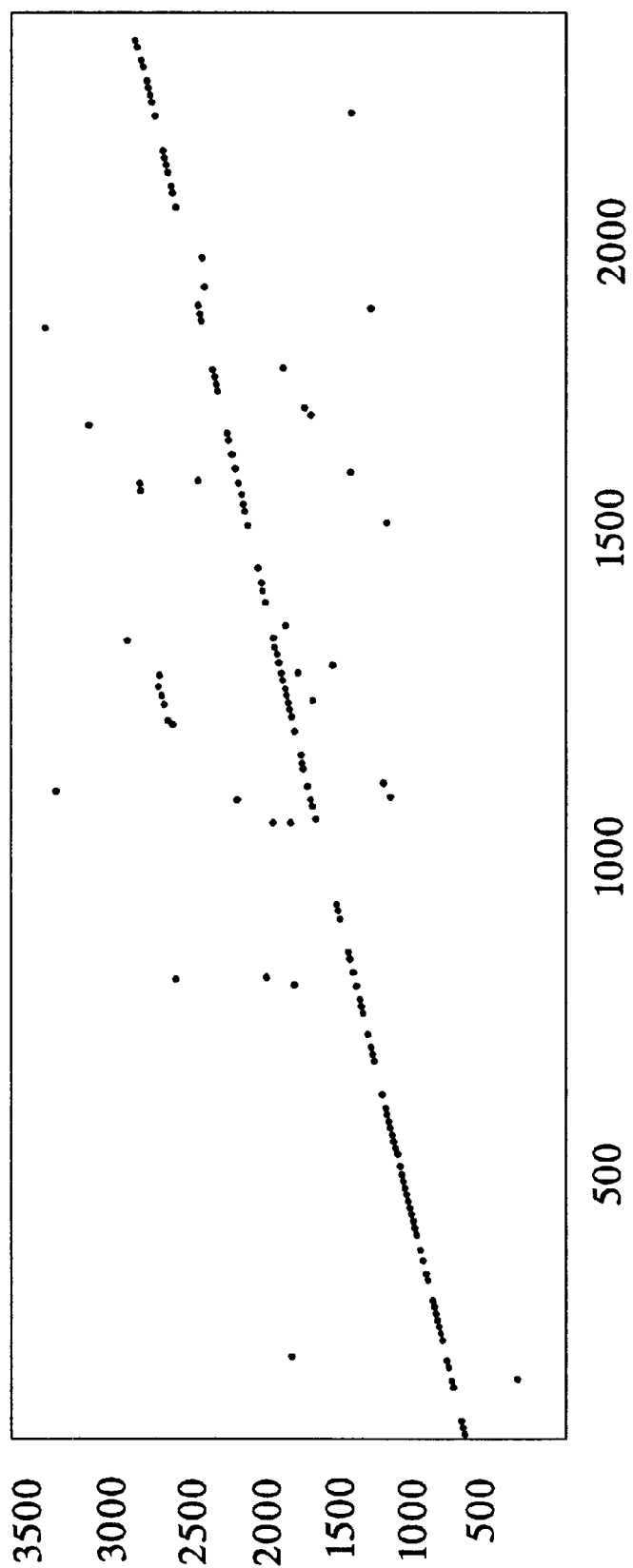
Figure 8D:
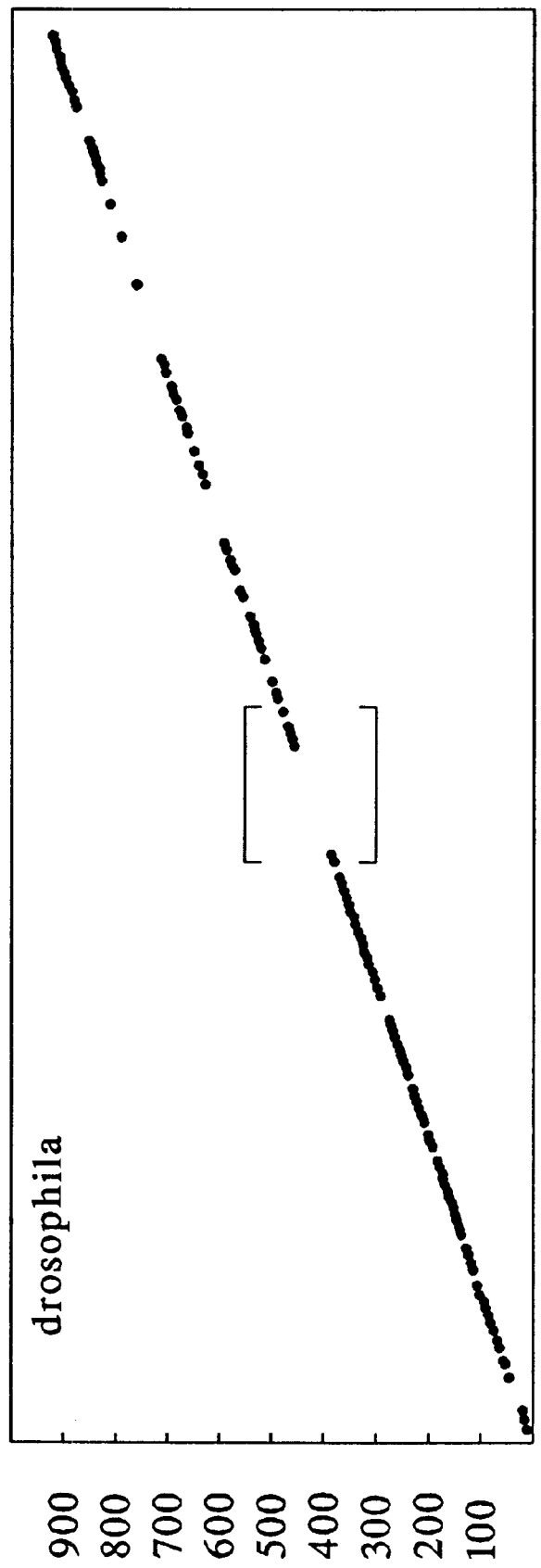

The ability of one of the anti-khcs GSE to induce etoposide resistance was further documented by using the isopropyl β-D-thiogalactopyranoside (IPTG)-inducible promoter/activator system, as described by Baim et al. (1991, Proc. Natl. Acad. Sci. USA 88: 5072–5076). The components of this system include an enhancer-dependent promoter, combined in cis with multiple repeats of the bacterial lac operator, and a gene expressing LAP265, an artificial regulatory protein derived from the lac repressor and a mammalian transcriptional activator. The anti-khcs GSE was cloned into the plasmid pX6.CLN, which contains the inducible promoter used by Baim et al., supra (a gift of Dr. T. Shenk) which expresses the inserts from an enhancerless SV40 early gene promoter supplemented with 21 repeats of the lac operator sequence. The resulting plasmid, which contains no selectable markers, was co-transfected into NIH 3T3 cells together with the LNCX plasmid carrying the neo gene. The mass population of G418- selected transfectants, along with control cells transfected with the insert-free vector, was exposed to increasing concentrations of etoposide, in the presence or in the absence of 5 mM IPTG. Even though the co-transfection protocol usually leads to the integration of the GSE in only a fraction of the G418-resistant cells, transfection with anti-khcs resulted in a clearly increased etoposide resistance, which was dependent on IPTG (see FIG. 5B).

EXAMPLE 4

Sequence Analysis of GSEs Conferring Resistance to the Chemotherapeutic Drug Etoposide The GSE anti-khcs, cloned as described in Example 3, was sequenced by the standard dideoxy sequencing procedure, and the deduced sequence is shown in FIG. 6. The nucleotide sequence of the "sense" and "antisense" strands, as well as amino acid sequence of the predicted peptides encoded by each of these strands, were analyzed for homology to the nucleic acid and protein sequences present in the National Center for Biotechnology Information data base, using the BLAST network program for homology search. The sequence corresponding to the "antisense" strand of the anti-khcs GSE, showed strong homology with several genes encoding the heavy chain of kinesins, a family of microtubule motor proteins involved in intracellular movement of organelles or macromolecules along the microtubules of eukaryotic cells. The highest homology was found with the human kinesin heavy chain (KHC) gene, as described by Navone et al. (1992, J. Cell Biol. 117: 1263–1275). Anti-khcs therefore encodes antisense RNA for a mouse khc gene, which we have termed khcs for khc associated with sensitivity (to drugs) or senescence. We refer to the kinesin molecule, formed by the associate of the KHCS protein with kinesin light chains, as kinesin-S, to distinguish it from the other kinesins present in mammalian cells. These results demonstrate that chemotherapeutic drug selection for GSEs can lead to the discovery of novel genetic elements, and can also reveal roles of genes in drug sensitivity that had never before been suspected.

EXAMPLE 5

Cloning and Analysis of the Gene from Which Anti-khcs GSE Gene was Derived

The anti-khcs GSE isolated in Example 3 was used as a probe to screen 400,000 clones from each of two cDNA libraries in the lambda gt10 vector. These libraries were prepared by conventional procedures from the RNA of mouse BALB/c 3T3 cells, either unsynchronized or at $G_0 \rightarrow G_1$ transition, as described by Lau and Nathans (1985, EMBO J. 4: 3145–3151 and 1987, Proc. Natl. Acad. Sci. USA 84: 1182–1186, a gift of Dr. L. Lau). Screening of the first library yielded no hybridizing clones, but two different clones from the second library were found to contain anti-khcs sequences. These clones were purified and sequenced. Sequence analysis showed that we have isolated the bulk of the mouse khcs cDNA, corresponding to 796 codons (the full-length human KHC cDNA encodes 963 amino acids). This sequence is shown in FIGS. 7A through 7C, an additional 252 nucleotides encoding 84 amino acids from the amino terminus have been determined from 5'-specific cDNA isolated using the "anchored PCR" technique, as described by Ohara et al. (1989, Proc. Natl. Acad. Sci. USA 86: 5763–5677). Additional missing 3'terminal sequences are currently being isolated using this technique.

The dot-matrix alignment of the sequenced portion of the khcs protein with previously cloned KHC proteins from the human (see Navone et al., 1992, J. Cell, Biol. 117: 1263–1275), mouse (see Kato, 1991, J. Neurosci. 2: 704–711), Drosphila (McDonald & Goldstein, 1990, Cell 61: 991–1000), and squid (see Kosik et al., 1990, J. Biol. Chem. 265: 3278–3283) is shown in FIGS. 8A through 8D. The portion corresponding to the anti-khcs GSE, is shown in brackets. The khcs gene is most highly homologous to the human gene (97% amino acid identity), suggesting that the human KHC (KHCS) gene is functionally equivalent to the mouse khcs. The alignment also shows that the anti-khcs GSE corresponds to the region which is the most highly diverged between different kinesins (shown in the Figure by brackets around these sequences).

EXAMPLE 6

Generation of a Random Fragment KHCS cDNA Retroviral Library and Isolation of KHCS-derived GSEs As described in Example 5 above, the murine khcs gene is highly homologous to the human KHC (or KHCS) gene described by Navone et al., (1992, J. Cell Biol, 117: 1263–1275). The functional equivalence of these genes was also suggested by the observation that the levels of KHCS mRNA are decreased in human cells selected for etoposide resistance (see Example 8). To determine conclusively that the human KHCS gene represents the functional equivalent of the mouse khcs, it was determined whether any random fragment of human KHCS cDNA could function as an etoposide-resistance GSE.

Figure 9A:
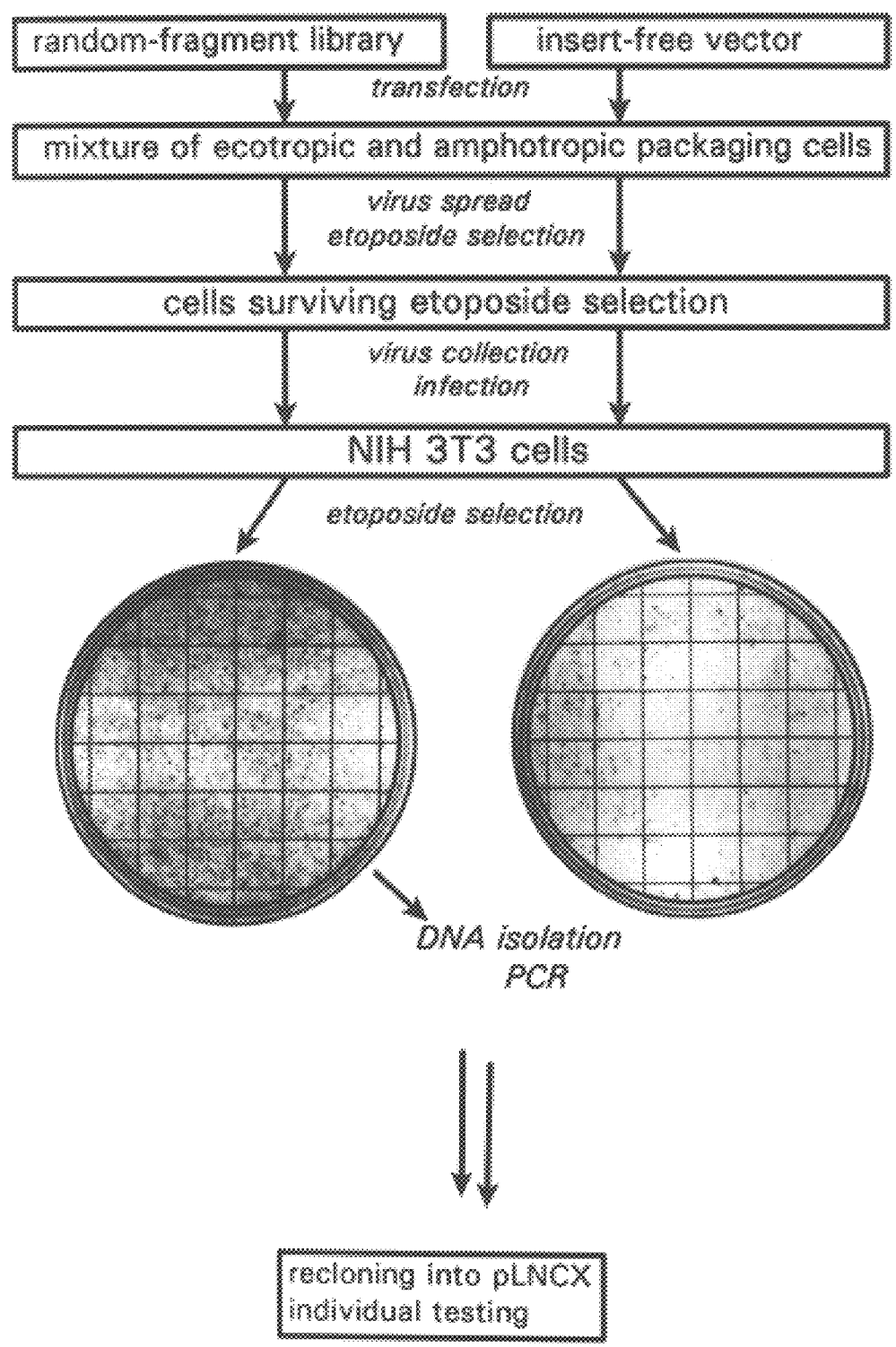

A library of random DNAaseI-generated fragments of a full-length human KHCS cDNA (2.9 kb in length; provided by Dr. R. Vale, University of California at San Francisco) was generated essentially as described above for topoisomerase II cDNA (see Example 1 in co-pending U.S. patent application Ser. No. 08/033,086, incorporated by reference), using the protocol illustrated in FIG. 9A, with the following modifications. Specifically, two synthetic adaptors, instead of one, were used for ligation with DNAase I-generated cDNA fragments. One adaptor, containing three ATG codons, carried a HindIII cloning site (FIG. 9B). The other adaptor had translation stop codons in all three reading frames and carried a ClaI cloning site (FIG. 9B). After ligation with the equimolar mixture of both adaptors, cDNA fragments were amplified by PCR using sense and antisense strands of the first and second adaptor, respectively. PCR products were digested with ClaI and HindIII and cloned into the corresponding sites of the pLNCX plasmid. This modification of the cloning strategy resulted in avoiding the formation of inverted repeats at the ends of the cDNA inserts after cloning into the retroviral vector.

Figure 10:
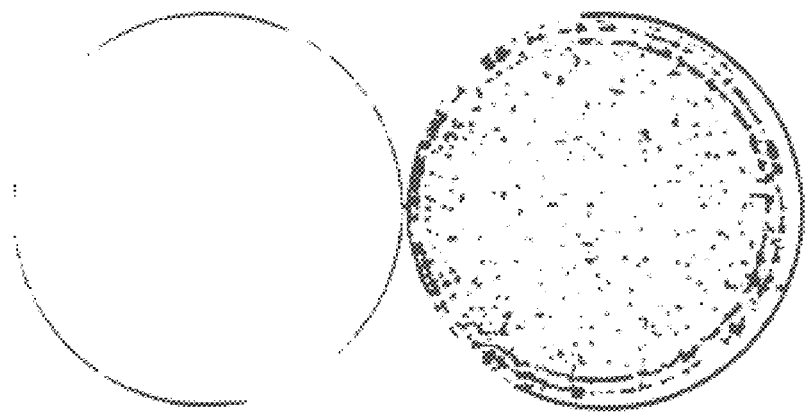
FIG. 10 shows etoposide resistance in HT1080 cells carrying insert-free vector virus or a random fragment library of human KHCS cDNA.

A plasmid library of 20,000 independent insert-carrying clones was obtained and transfected into ecotropic packaging cells using the calcium phosphate precipitation technique. Virus released by transiently transfected cells was used to infect HT 1080/pJET-2TGH cells, clone 2, a derivative of human HT1080 fibrosarcoma cell line transfected with a plasmid expressing the murine ecotropic receptor (Albritton et al., 1989, Cell 57: 659–666) and susceptible to infection with ecotropic retroviruses (provided by Dr. G. R. Stark, Cleveland Clinic Foundation). After infection and G418 selection, these cells (further referred to as HT1080/ER) were plated at $10^5$ cells per 100 mm plate and cultivated for 12 days in different concentrations of etoposide (200–500 ng/mL). After removal of the drug, cells were allowed to grow in media without drug for 7 more days. At this point, some of the plates were fixed and stained with crystal violet, to determine the number of surviving colonies. (FIG. 10). As illustrated in FIG. 10 at drug concentrations 250 ng/mL etoposide, there were only several colonies in control plates, compared with about a hundred times more colonies in the plates containing GSE-containing cells.

In a parallel experiment, virus-producing mixtures of packaging cells were subjected to similar etoposide selection. At all drug concentrations tested, there were many more colonies surviving etoposide treatment in the GSE-carrying cells than in the control cell population.

These results indicated that the retroviral library of random fragments of KHCS cDNA contained numerous GSEs inducing drug resistance in human cells, confirming that human KHCS is associated with drug resistance. Some of these GSEs are likely to be more potent as selectable markers of drug resistance that the original single GSE from the murine khcs gene. The virus isolated from such etoposide-resistant cells represents a collection of a multiplicity of kinesin-derived, drug resistance-conferring GSEs, which multiplicity is itself an aspect of the present invention and is useful in conferring resistance to DNA damaging agents, including chemotherapeutic drugs, as disclosed herein.

EXAMPLE 7

Generation of Cell Populations Carrying Multiple Copies of anti-khcs GSEs

A 1:1 mixture of ecotropic and amphotropic packaging cells was transfected with retroviral vector pLNCX carrying the anti-khcs GSE using a standard calcium phosphate procedure. Two weeks later, the virus titer, as measured by the formation of G418- resistance NIH 3T3 colonies, reached >$10^6$ infectious units per mL as a result of "ping-pong" infection (see Bodine et al., 1990, Proc. Natl. Acad. Sci. USA 87: 3738–3742). This virus-containing supernatant was used to infect NIH 3T3 cells, 10 times with 12 hour intervals. Control cells were infected in parallel with the insert-free vector virus obtained by the same procedure. G418 selection showed that 100% of NIH 3T3 cells became infected with the virus. DNA from the infected cells was analyzyed by Southern blot hybridization with a virus-specific probe. This analysis showed that the infected cells contained multiple copies of the integrated provirus.

Freshly-obtained multiply-infected NIH 3T3 cells were characterized by a decreased growth rate and plating efficiency. After several passages, however, their growth parameters became indistinguishable from the control cells, suggesting the elimination of slowly growing cells from the population. At this stage, the cells were frozen and used for the experiments described below.

EXAMPLE 8

Figure 11A:
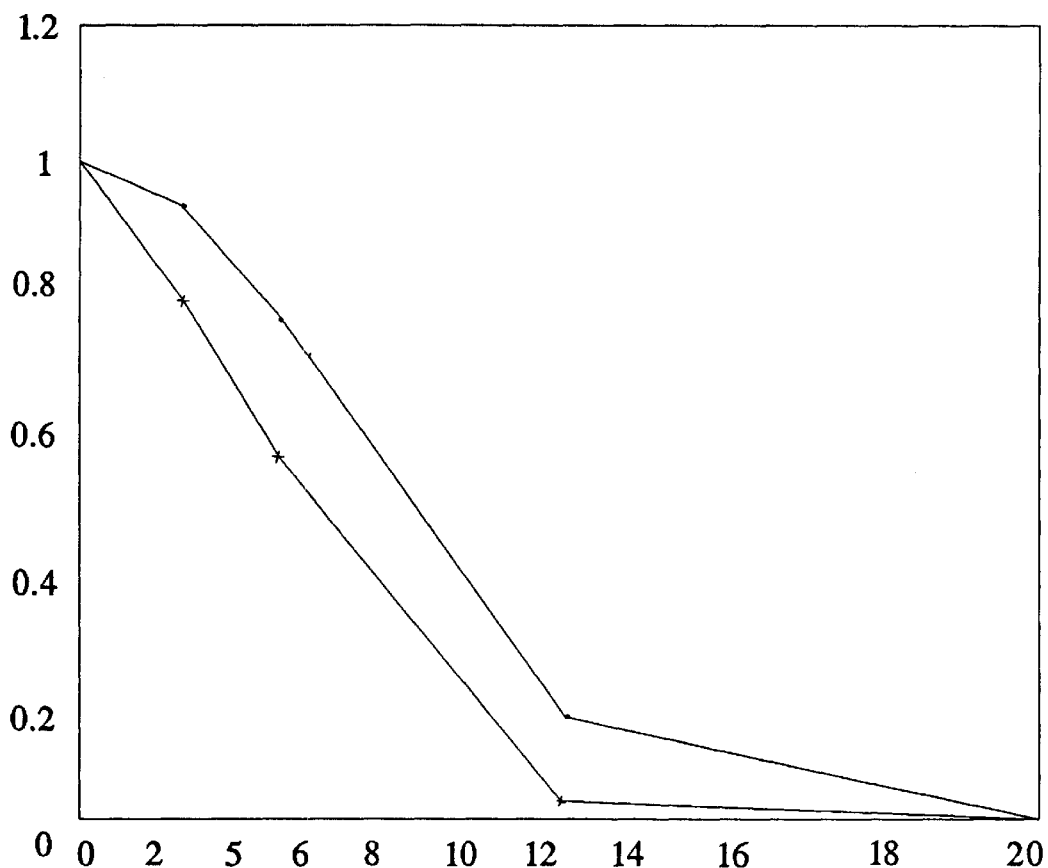
FIGS. 11A through 11G shows the effects of different drugs on 4-day growth of NIH 3T3 cells infected with insert-free vector virus or with a virus encoding anti-khcs. Cell growth in the absence of the drug differed less than 5% for the compared populations. Drug concentrations are given in ng/mL. A representative series of parallel assays, carried out in triplicate, is shown.
Figure 11B:
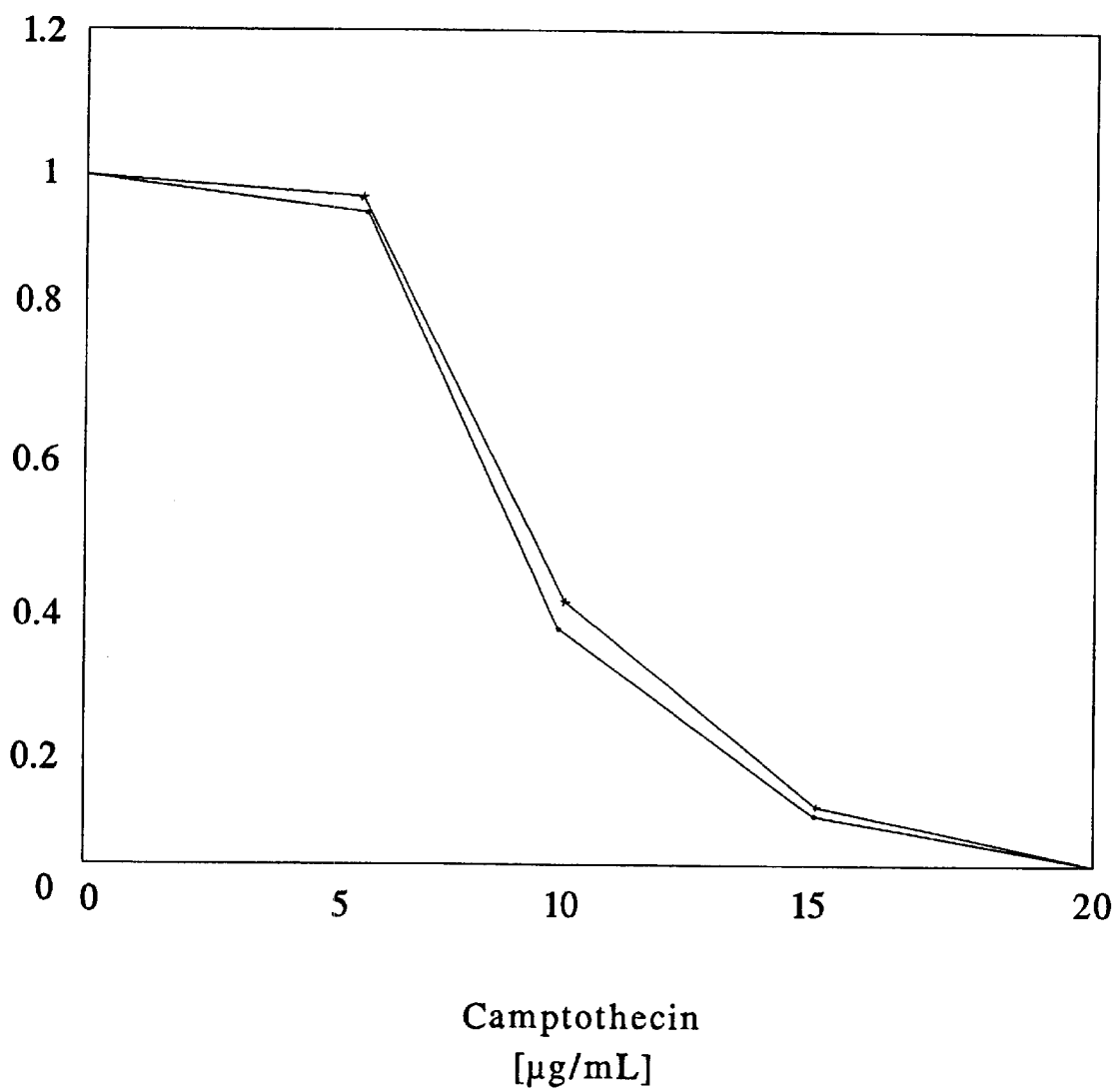
Figure 11C:
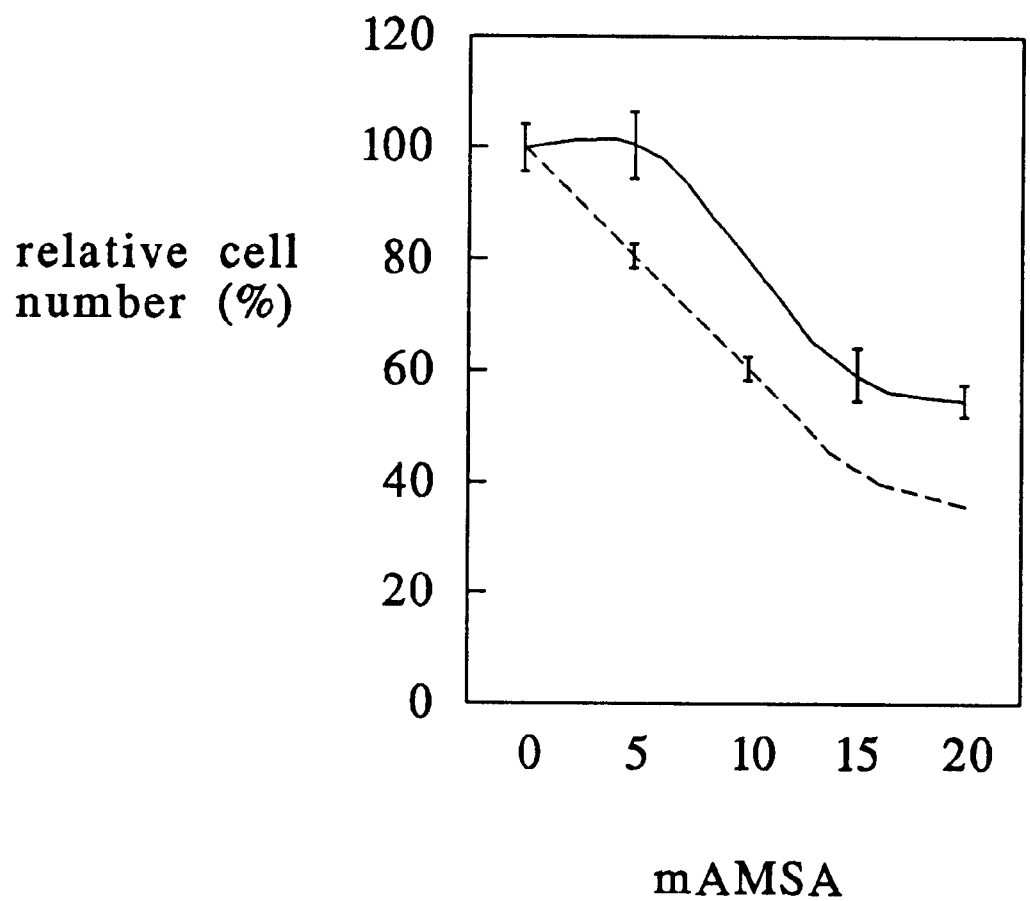
Figure 11D:
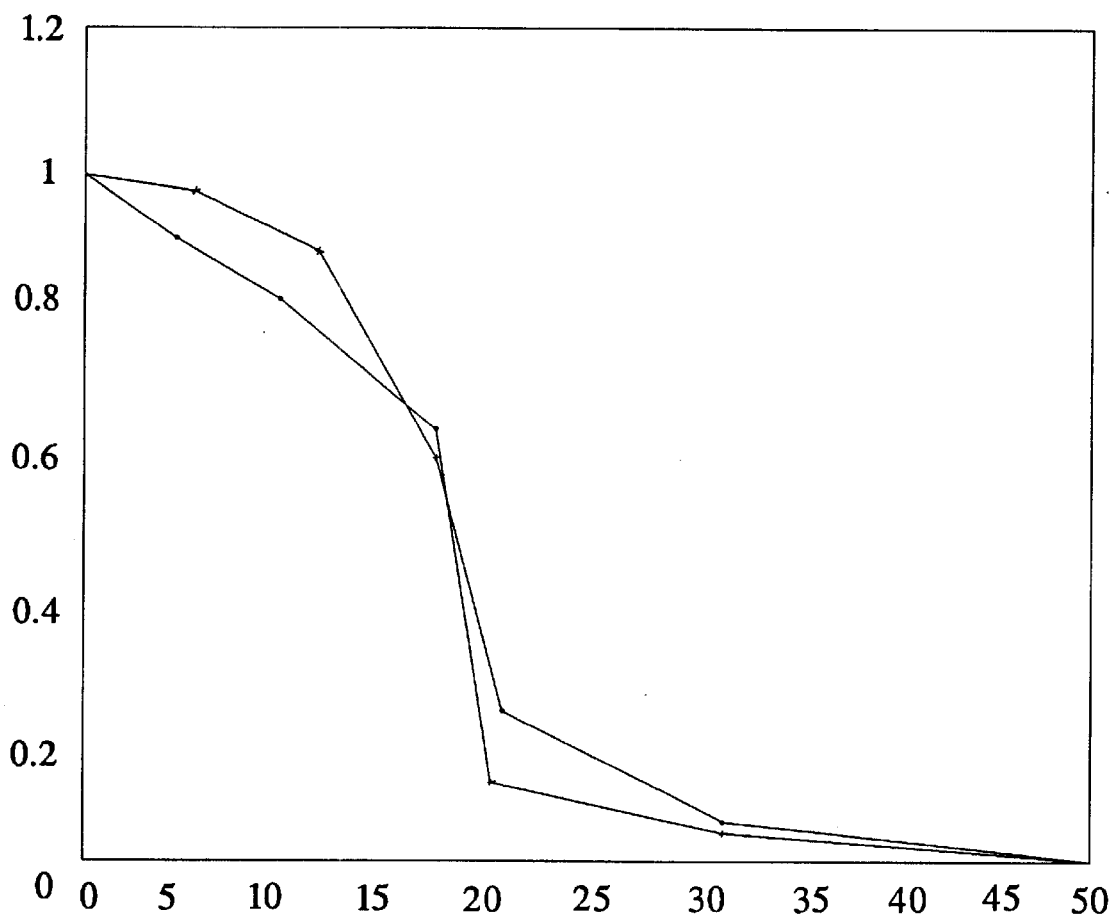
Figure 11E:
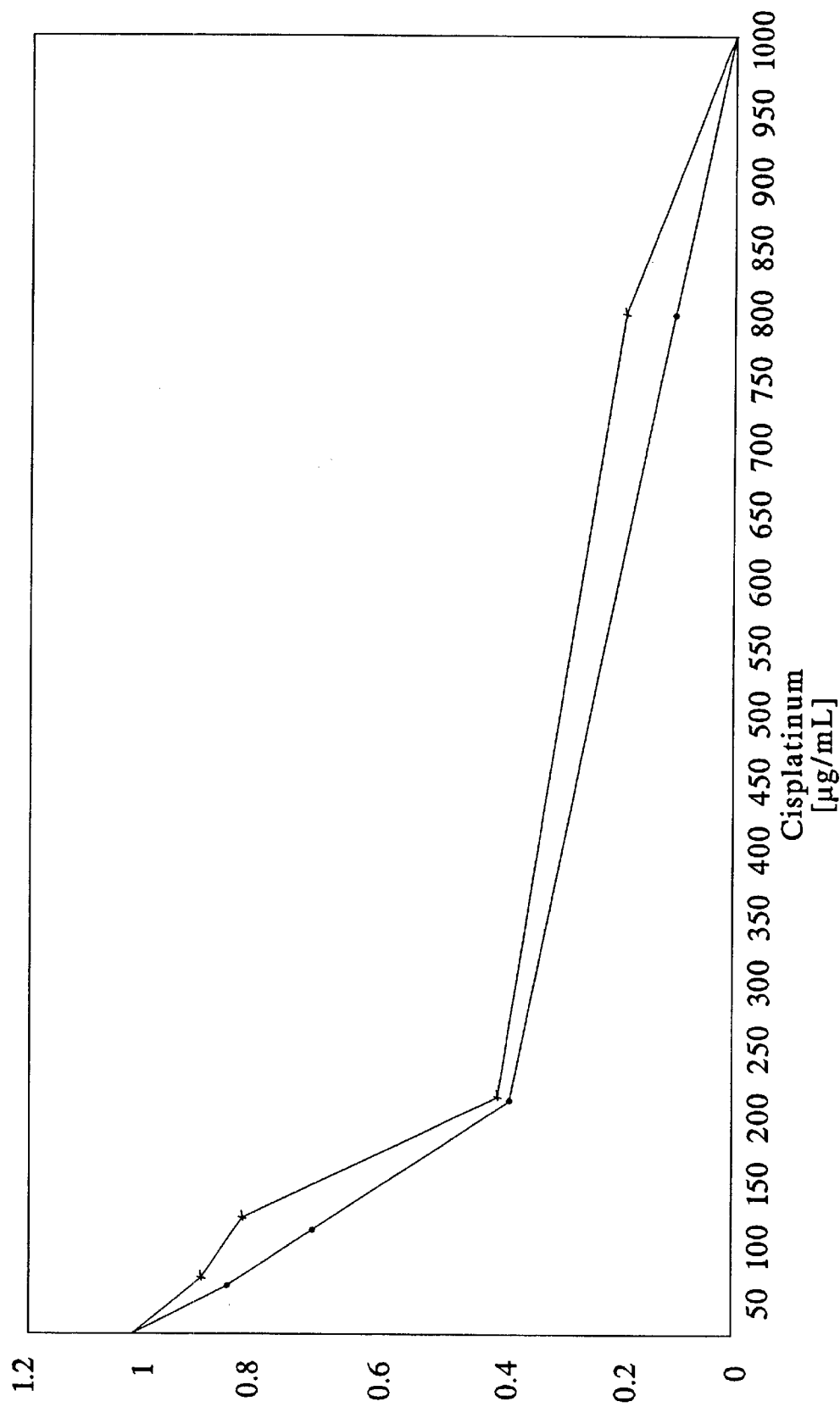
Figure 11F:
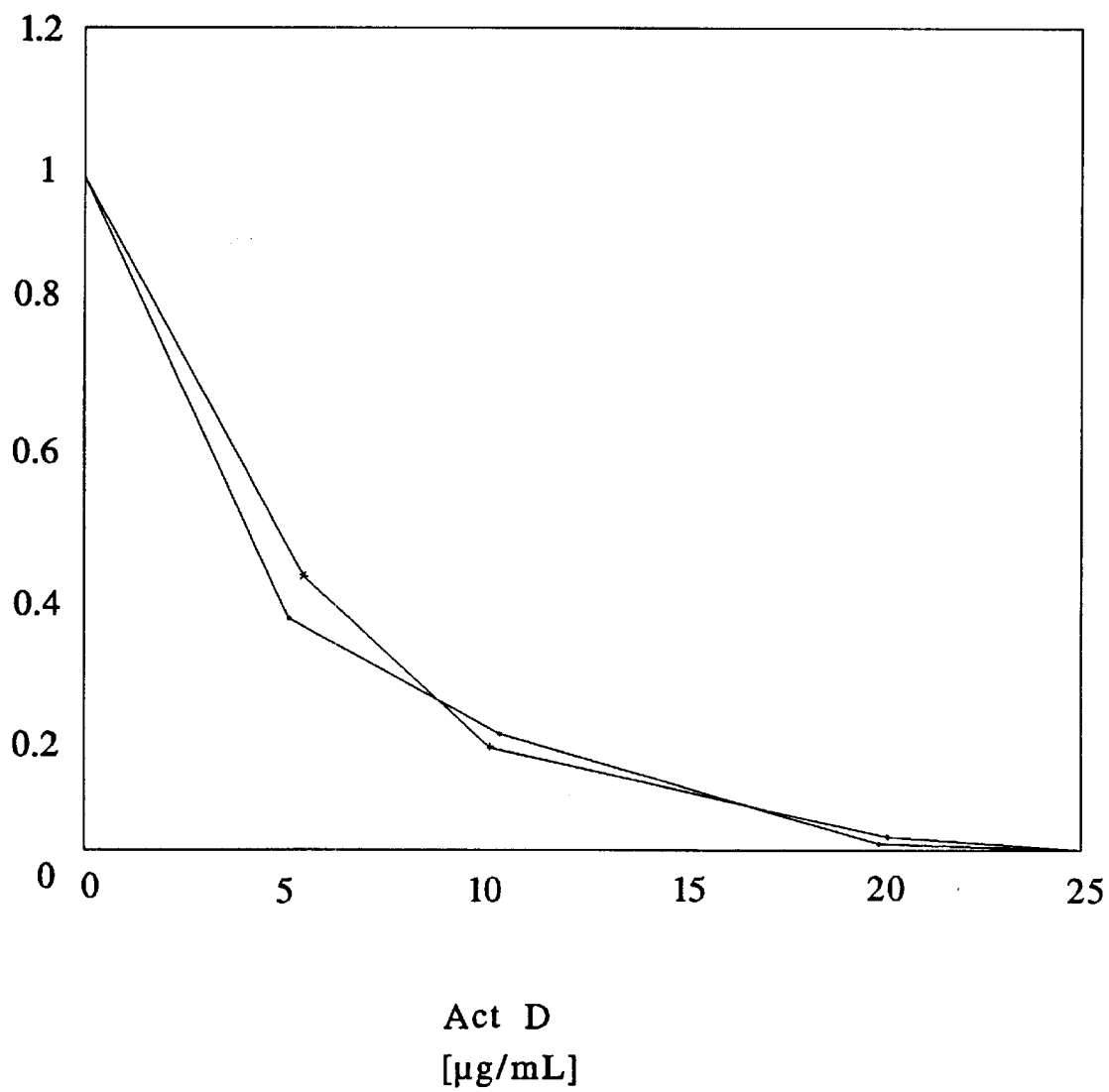
Figure 11G:
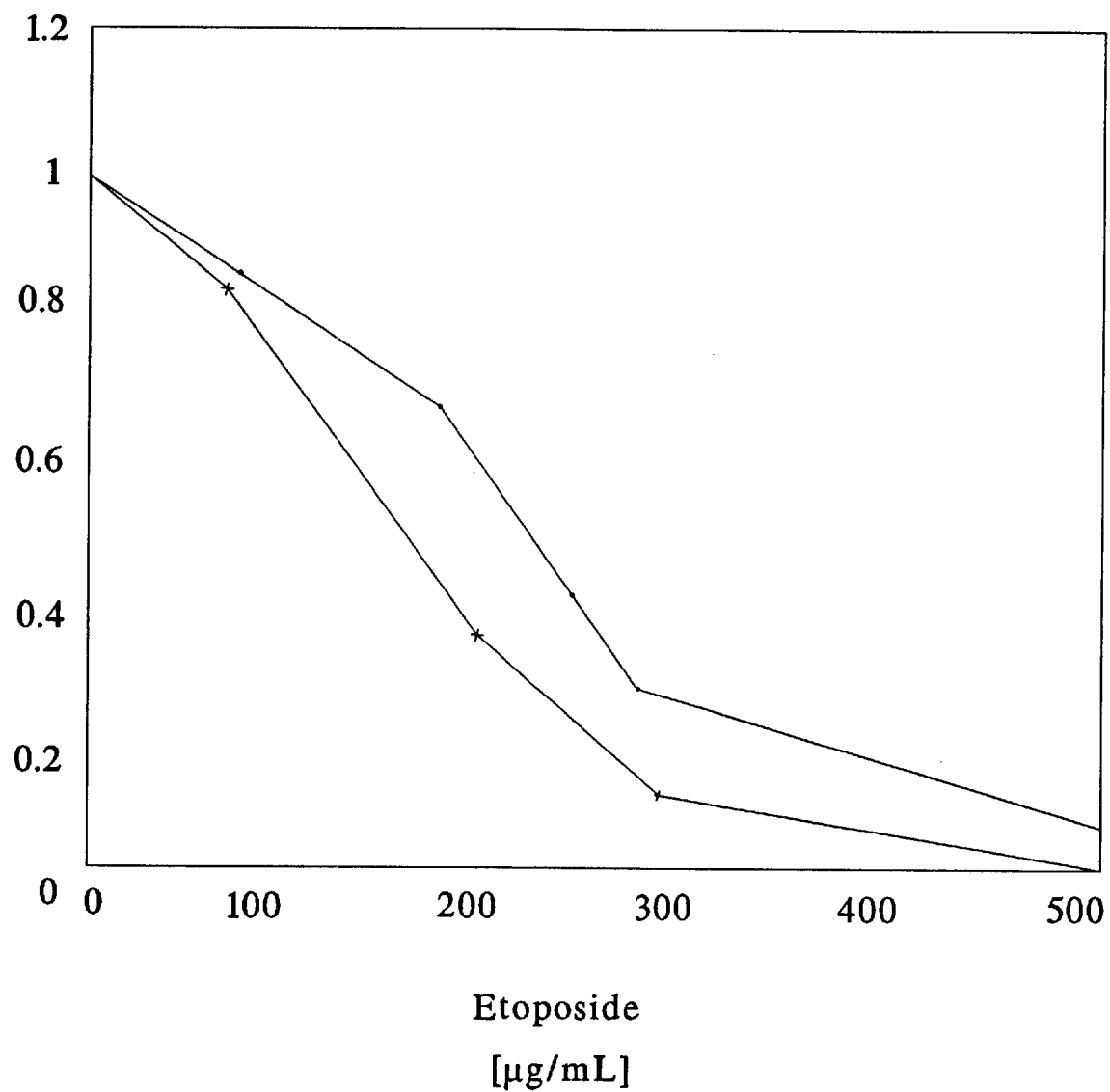

Drug Resistance Pattern of NIH 3T3 Cells Carrying Multiple Copies of Anti-khcs GSEs The infected cell population described in Example 7 were analyzed for resistance to several anticancer drugs by a growth inhibition assay. For this assay, $10^4$ cells per well were plated in 12-well plated and exposed to increasing concentrations of different drugs for 4 days. Relative cell numbers were measured by the methylene blue staining assay (Perry et al., 1992, Mutation Res. 286: 189–197). Despite the relative insensitivity of this assay when carried out with unselected heterogeneous cell populations, infection with the virus carrying an anti-khcs GSE induced a pronounced increase in the resistance to the cytostatic effects of etoposide and amsacrine and, to a lesser extent, of Adriamycin camptothecin and cisplatin FIGS. 11A through 11C, FIG. 11E and FIG. 11G. All of these drugs are known to induce DNA damage, albeit by different mechanism. Under the same assay conditions, no increase in resistance was observed with colchicine or actinomycin FIGS. 11D and 11F.

To further characterize the nature of drug resistance conferred by anti-khcs, the above-described short-term growth inhibition assays were followed by long-term growth inhibition assays which measured both the cytostatic and the cytotoxic effects of different drugs. These assays were carried out by incubating the cells for four days in the presence of the drugs, followed by either two or six days in the absence of the drug, to allow for programmed cell death, which is frequently associated with recovery from drug-induced inhibition (Kung et al., 1990, Cancer Res. 50: 7307–7317). These assays showed that the GSE-carrying cells were resistant to etoposide and adriamycin, but not to cisplatin, camptothecin or actinomycin D. Furthermore, the GSE-carrying cells were found to be hypersensitive to colchicine and vinblastine, said hypersensitivity being increasingly more evident with increasing length of the assay.

Figure 12A:
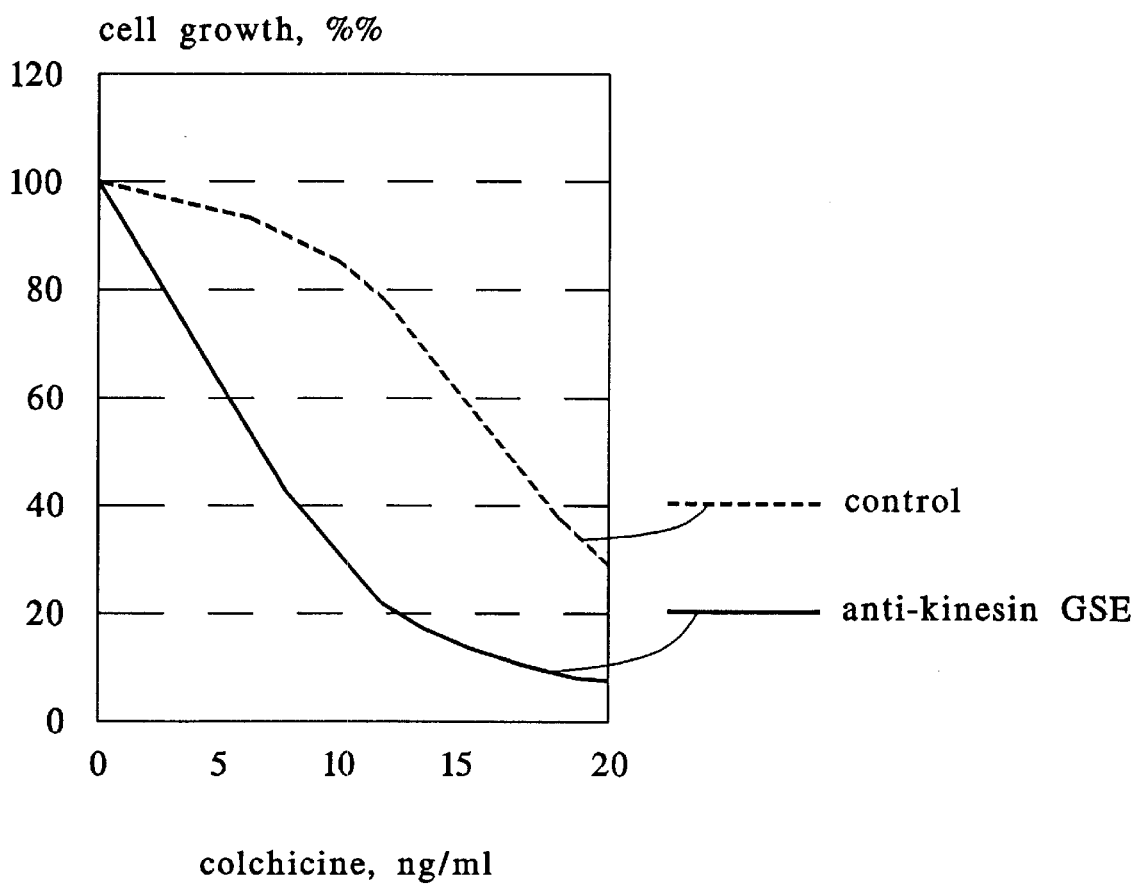
FIGS. 12A and 12B shows growth of cells carrying anti-khcs (solid lines) and control cells (broken lines) after treatment with colchicine or vinblastine. Cells were incubated with the drugs for 4 days, followed by 2 or 4 days in drug-free media, as indicated. Cell growth, presented in arbitrary units, was evaluated by methylene blue staining.
Figure 12B:
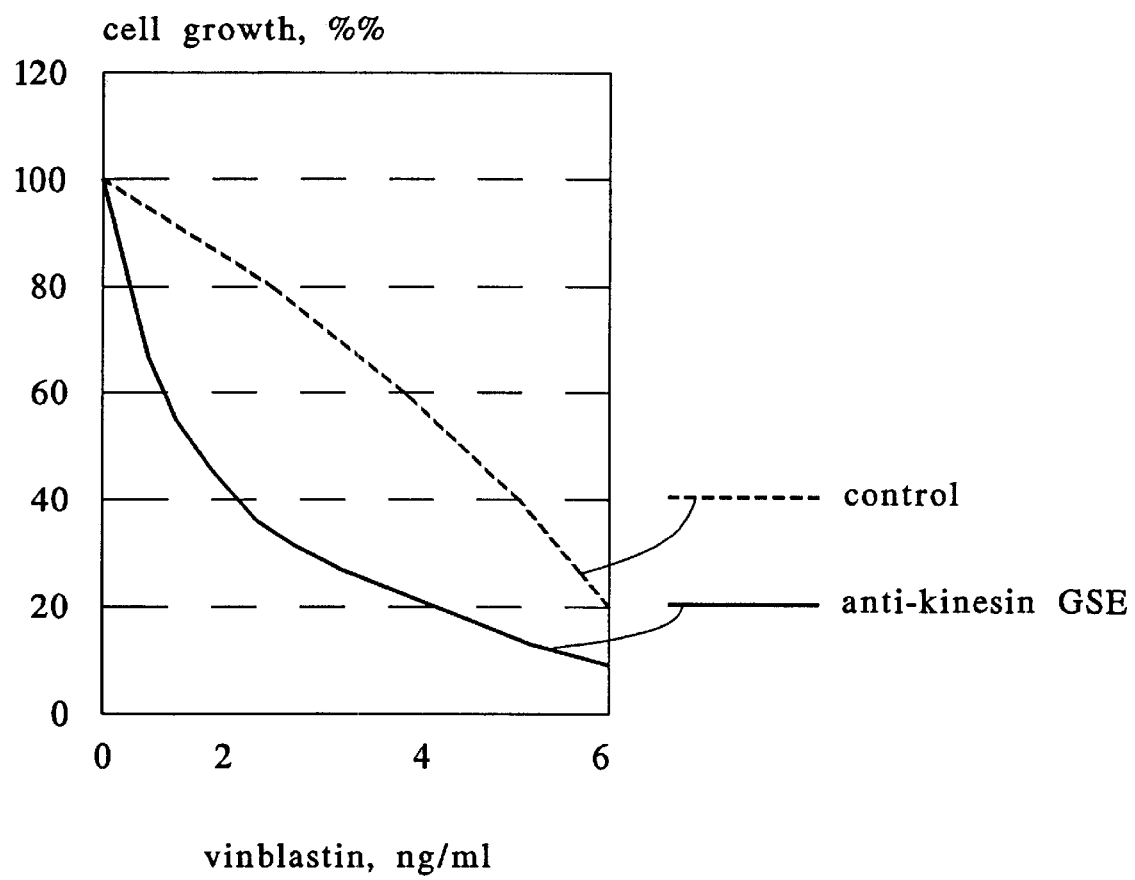

Thus, in the experiment shown in FIGS. 12A and 12B, NIH 3T3 cells carrying the anti-khcs GSE and control cells without the GSE were plated at a density of $2 \times 10^4$ per culture dish and grown for five days in concentrations of either colchicine or vinblastine. The cells were then fixed and stained, and the number of surviving cells determined and shown as a percentage of cell growth in the absence of drug. These results clearly show that expression of the anti-khcs GSE in these cells was accompanied by hypersensitivity to both colchicine and vinblastine.

To further investigate the discrepancy between the results obtained in the short-term and long-term drug assays, analyses of the dynamics of cell growth during and after treatment with 250 ng/mL etoposide, 20 ng/mL camptothecin and 40 ng/mL colchicine were performed. In these experiments (shown in FIGS. 13A through 13D), NIH 3T3 cells were treated with the corresponding drugs for 5 days, and then incubated for additional 6 days either in the presence or in the absence of the drug. The selected drug concentrations resulted in growth inhibition but little detectable cell death in continuous presence of the drug. After 11 days of drug exposure the total cell number in the etoposide- or camptothecin-treated populations of control cells was a little lower than after 5 days of drug exposure, but in the colchicine-treated control cell population a slow cell growth was still detectable. In the experiments where the drug was removed after 5 days, cell growth was initially activated for all three drugs. After about two days of growth in the absence of the drug, the number of cells treated with etoposide or camptothecin decreased, however, due to extensive cell death, so that the final cell number in cell populations incubated in the absence of the drugs was practically the same as in the cells continuously maintained in the presence of colchicine or camptothecin. In contrast, cells pre-treated with colchicine undergo only limited cell death after removal from the drug, resulting in a relatively minor slowdown in cell growth tow days after removal from the drug, resulting major increase in the total cell number in the populations removed from the drug relative to those that were constantly maintained in colchicine FIGS. 13A through 13D.

Figure 13A:
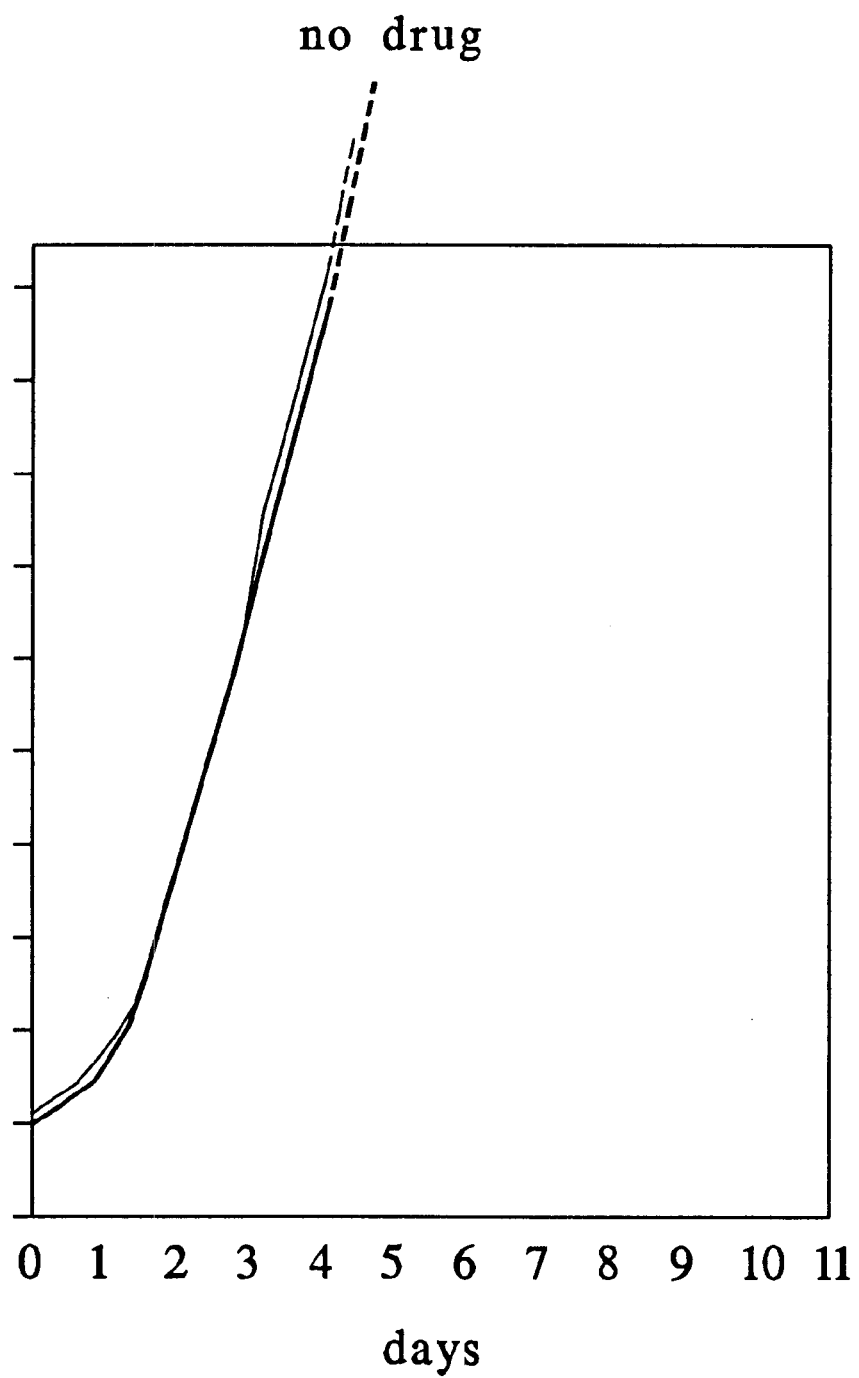
FIGS. 13A through 13D shows a kinetic analysis of cell growth of anti-khcs GSE-carrying cells (black lines) and control cells (grey lines) incubated with different drugs. Cell growth was measured as described for FIGS. 12A and 12B. Cells were plated and one day later (indicated by the first arrow) the indicated drugs were added at concentrations as described. Four days later (indicated by the second arrow), the drugs were removed from some of the plates. Solid lines indicate cell growth in the continuous presence of the drug, and broken lines indicate cell growth after removal of the drug.
Figure 13B:
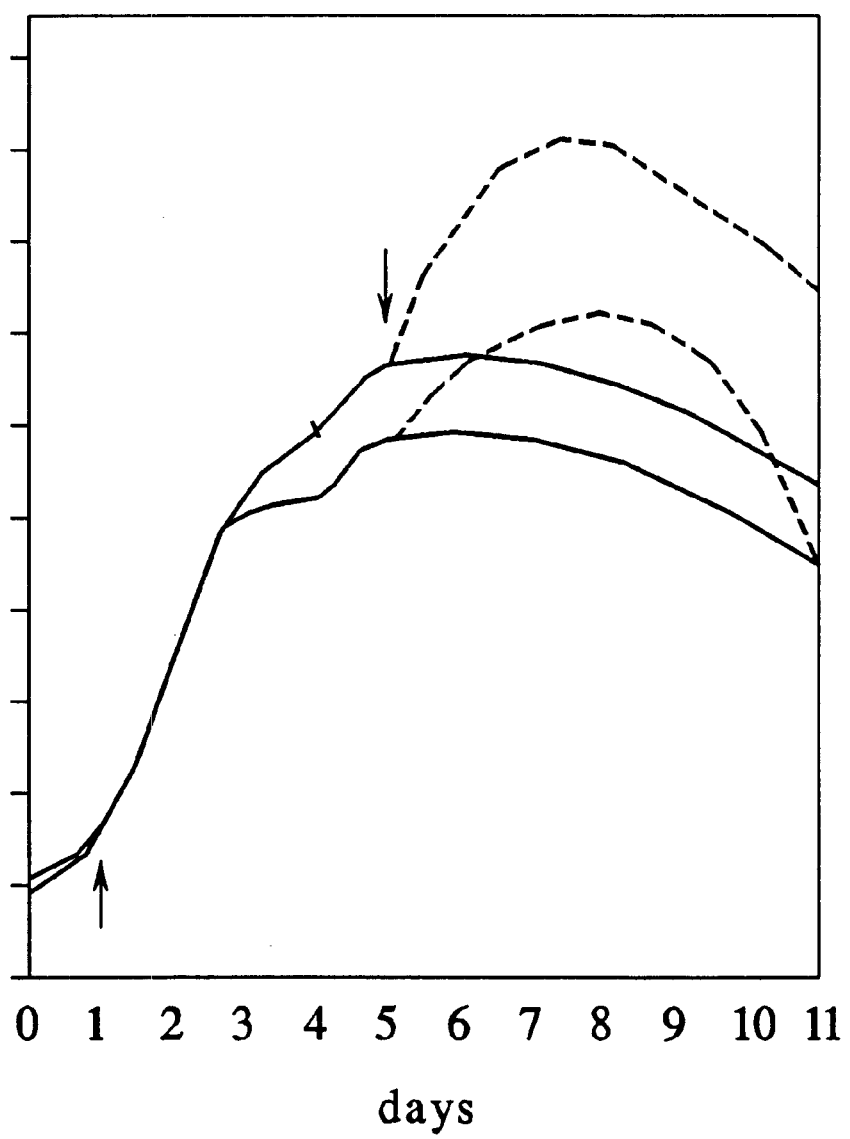
Figure 13C:
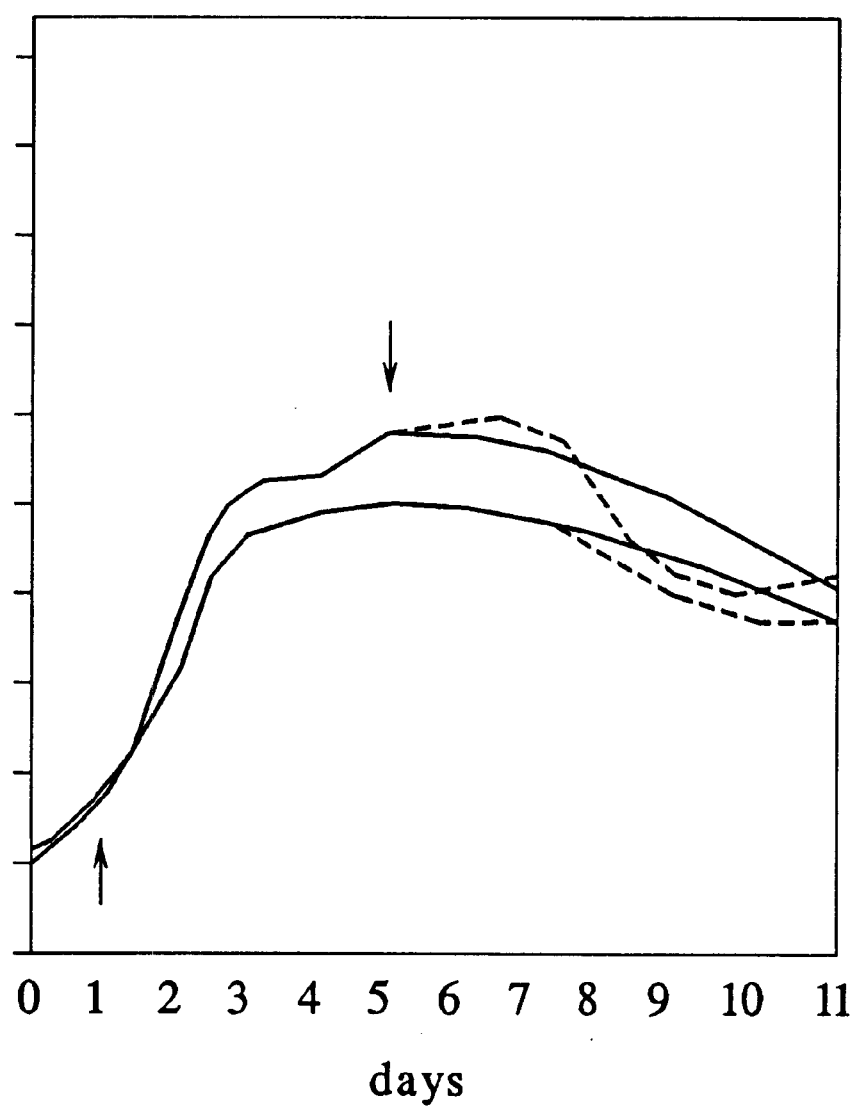
Figure 13D:
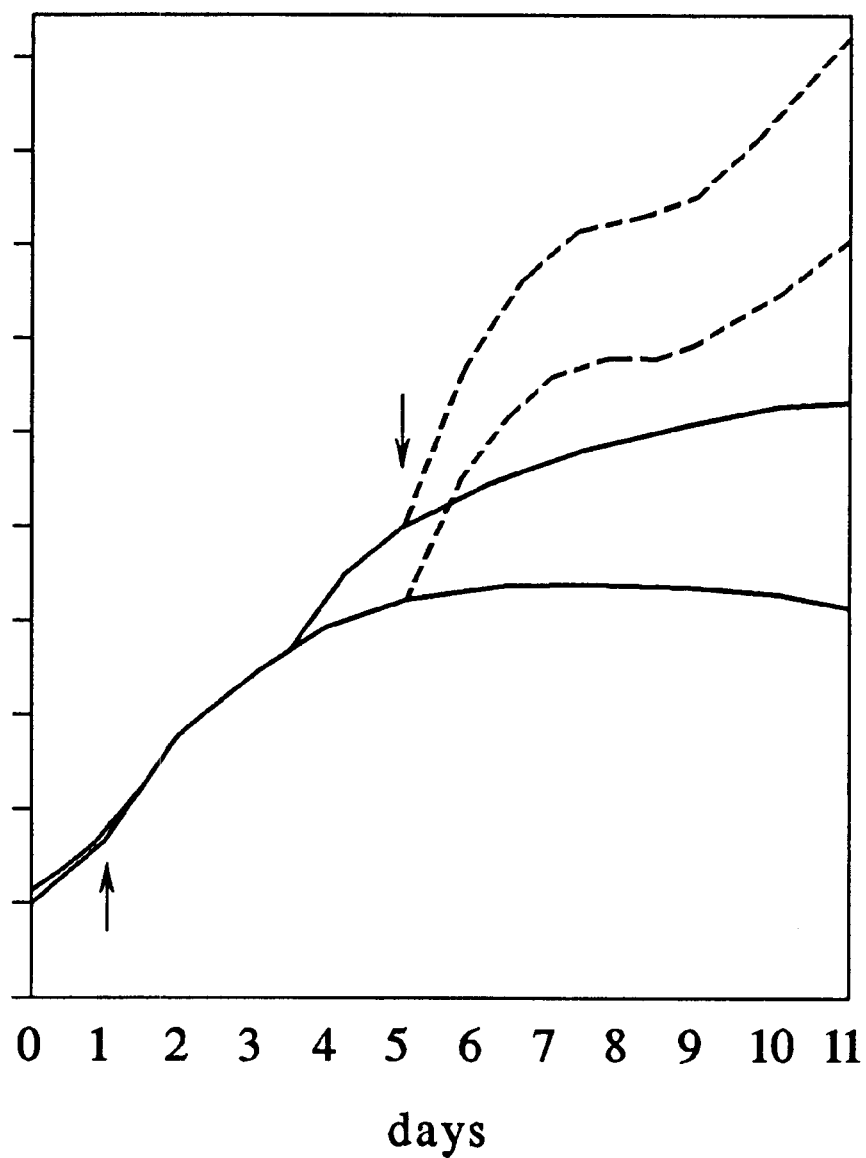

The expression of the anti-khcs GSE had different effects on the growth inhibition and recovery-associated cell death induced by these drugs. In cells treated with etoposide, anti-khcs decreased the growth-inhibitory effect of the drug to the same, relatively small extent after 5 or 11 days of continuous exposure. In addition, the anti-khcs GSE decreased the amount of cell death in the populations released from etoposide inhibition. As a result, the increase in etoposide resistance conferred by this GSE was much more pronounced after release from the drug than under the conditions of continuous exposure (FIG. 13B). In cells treated with camptothecin, the GSE resulted in a small decrease of the growth-inhibitory effect of the drug, which was more pronounced after 5 days of exposure but was reduced to negligible levels after 11 days of continuous exposure FIG. 13C. The decrease in growth inhibition after 5 days of exposure was accompanied by a slight increase in cell death after the removal from the drug, so that the GSE produced no significant long-term difference in camptothecin resistance. In the populations treated with colchicine, the anti-khcs GSE made cells more susceptible to the growth-inhibitory effect of the drug; this effect was increased with prolonged exposure and was equally apparent in the populations released from the drug after 5 days or continuously maintained in colchicine FIG. 13D.

The results of the above experiments indicated that the anti-khcs GSE acts by inhibiting the cytostatic effects of different DNA-damaging drugs. In addition, this GSE appears to decrease the extent of programmed cell death occurring after the release from the drug in cells treated with some (etoposide) but not other (camptothecin) DNA-damaging agents.

The finding that cells carrying the anti-khcs GSE become hypersensitive to the cytostatic effects of colchicine has potentially significant therapeutic implications. The observed hypersensitivity to colchicine, an anti-microtubular agent, in cells with GSE-mediated inhibition of kinesin is likely to be mechanically related to the essential functions of kinesin, which moves various structures along the microtubules and may be involved in the sliding of microtubules relative to each other, as well as the assembly and disassembly of microtubules. The pronounced effect of the anti-khcs GSE on the sensitivity of cells to anti-microtubule agents also indicates that this GSE affects the general kinesin function in the cells, and is not limited to a particular drug-response-specific isoform of kinesin. Since we have demonstrated that down-regulation of the KHCS gene represents a natural mechanism of drug resistance in human tumor cells (see Example 11), the hypersensitivity to colchicine provides an approach to overcoming this type of resistance in human cancer.

EXAMPLE 9

Assessment of Cellular Effects of Anti-kinesin GSEs

Figure 14:
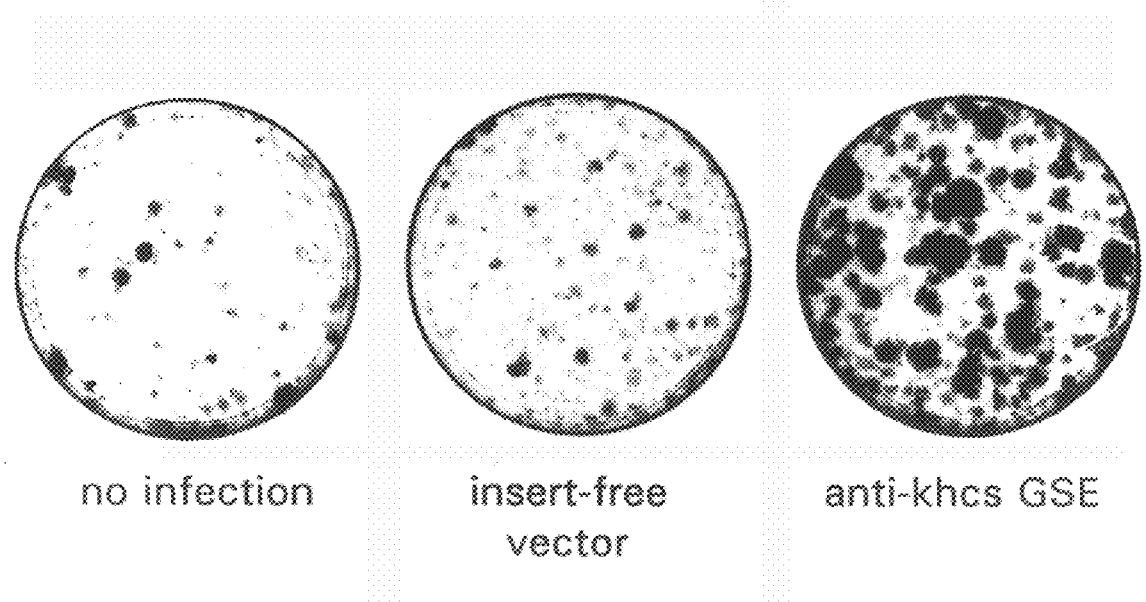
FIG. 14 demonstrates increased immortalization of primary mouse embryo fibroblasts by infection with the LNCX vector containing the anti-khcs GSE, relative to cells infected with the LNCX vector alone or uninfected (control) cells.

The virus carrying the anti-khcs GSE was treated for the ability to increase the life span of primary mouse embryo fibroblasts (MEF). MEF were prepared from 10 day old mouse embryos by a standard trypsinization procedure and senescent cells were frozen at different passages prior to crisis. Senescent MEF, two weeks before crisis, were infected with recombinant retroviruses carrying LNCX vector either without an insert or with anti-khcs. FIG. 14 shows MEF cell colonies two weeks after crisis. Relative to uninfected MEF cells, or cells infected with a control LNCX virus, cells infected with the anti-khcs showed a great increase in the proportion of cells surviving the crisis. Post-crisis cells infected with the anti-khcs virus showed no microscopically visible features of neoplastic transformation. These results indicate that anti-khcs promotes the immortalization of normal senescent fibroblasts. These results suggest that the normal function of kinesin-S may be associated with the induction of programmed cell death occurring after exposure to certain cytotoxic drugs or in the course of cellular senescence. These results also indicate that isolation of GSEs that confer resistance to chemotherapeutic drugs can provide insight into the cellular genes and processes involved in cell growth regulation.

EXAMPLE 10

Biological Effects of Mouse Anti-khcs GSE on Human Senescent Fibroblasts

The ability of the anti-khcs GSE described in Example 4 to promote immortalization of primary mouse embryo fibroblasts (demonstrated in Example 9) suggested that kinesin-S may act as a tumor suppressor by preventing immortalization of normal mouse fibroblasts. To determine if this gene may play the same role in human cells, the ability of the anti-khcs GSE to affect the life span of primary human fibroblasts was investigated.

Figure 15:
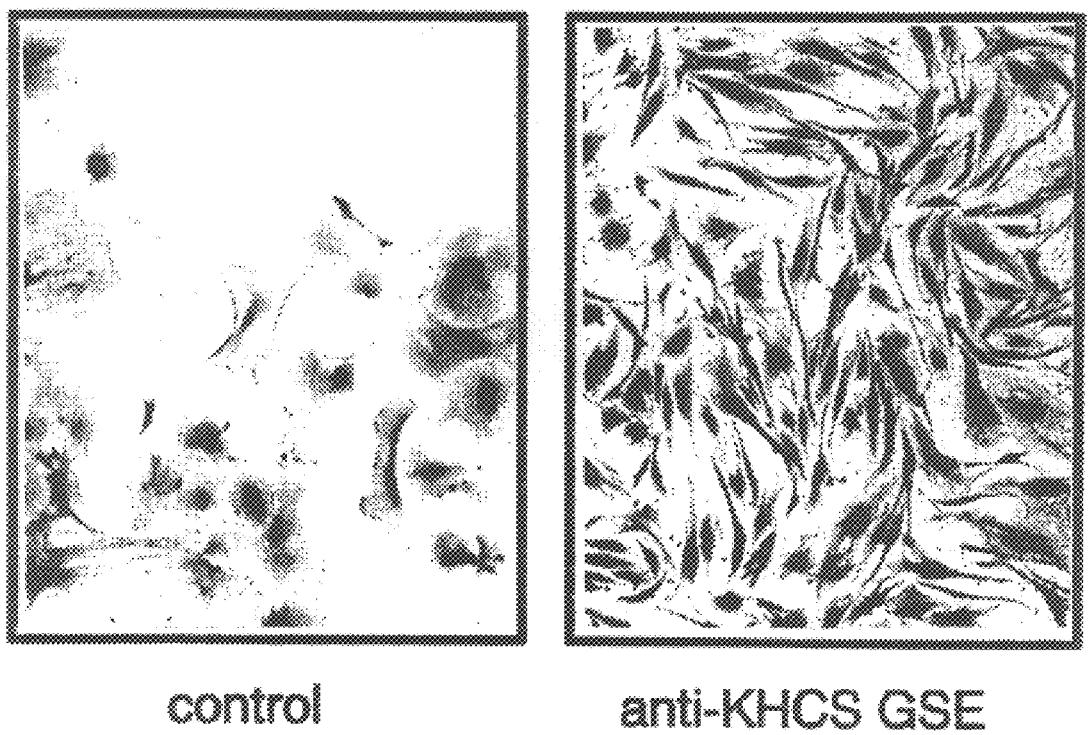
FIG. 15 demonstrates increased immortalization of primary human skin fibroblasts by infection with the LNCX vector containing the anti-khcs GSE (left panel) at the 4th passage after infection, relative to human skin fibroblasts in growth crisis (right panel).

Primary human fibroblasts, derived from human skin, were obtained from the Aging Cell Repository of the National Institutes of Aging. The cells were grown in DMEM with 20% fetal calf serum supplemented with twice the concentration of amino acids and vitamins normally used to supplement normal human skin fibroblast growth in culture. Cells at the fifth passage were infected with either the control pLNCX virus or the virus carrying mouse anti-khcs GSE (produced as described above in Example 3). Four passages later, the control cells went into crisis, but GSE-carrying cells continued to grow (FIG. 15) and have so far survived at least five additional passages. These results demonstrated that the anti-khcs GSE of this invention is also capable of prolonging life span of primary human fibroblasts, indicating that KHCS is a potential tumor suppressor in human cells.

EXAMPLE 11

Assessment of the Role of Decreased khcs Gene Expression in Naturally Occurring Mechanisms of Drug Resistance To test whether decreased khcs gene expression is associated with any naturally occurring mechanism of drug resistance, an assay was developed for measuring khcs mRNA levels by cDNA-PCR. This assay is a modification of the quantitative assay described by Noonan et al. (1990, Proc. Natl. Acad. Sci. USA 87: 7160–7164) for determining mdr-1 gene expression. The oligonucleotide primers had the sequences AGTGGCTGGAAAACGAGCTA (SEQ.ID.NO.:5) and CTTGATCCCTTCTGGTTGAT (SEQ.ID.NO.:6). These primers were used to amplify a 327 bp segment of mouse khcs cDNA, corresponding to the anti-khcs GSE. These primers efficiently amplified the mouse cDNA template but not the genomic DNA, indicating that they spanned at least one intron in the genomic DNA. Using these primers, we determined that khcs mRNA is expressed at a higher level in the mouse muscle tissue than in the kidney, liver or spleen.

Figure 16:
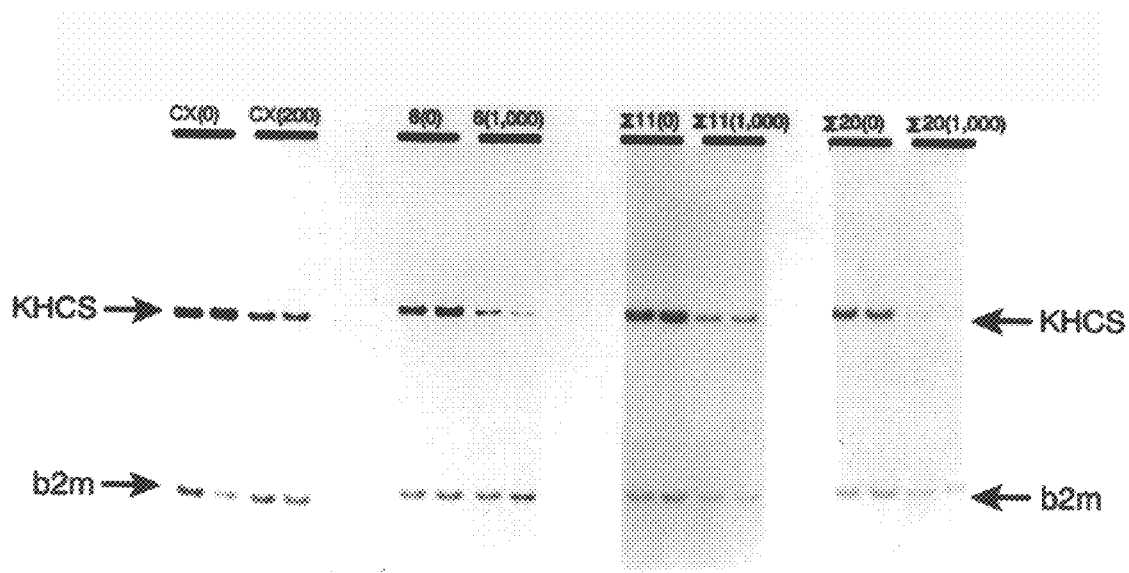
FIG. 16 shows cDNA-PCR quantitative analysis of expression of the human khcs gene in various unselected and etoposide-selected human HeLa cells. Lanes a shows results for clone CS(O), lands a' for clone CX(200), lanes b for clone Σ/11(O), lanes b' for clone Σ11 (1000), lanes c for clone 6(O), lanes c' for clone 6(1000), lanes d for clone Σ20(O) and lanes d' for clone Σ20 (1000). The numbers in parentheses for each clone name indicate the concentration of etoposide (ng/ml) present in the growth media. Bands indicative of khcs expression are shown along with bands for β-2 macroglobulin expression as an internal control.

In another experiment a pair of primers amplifying a homologous segment of the human KHCS cDNA was selected, based on the report human KHC sequence published by Navone et al. (1992, J. Cell. Biol. 117: 1263–1275). The sequences of these primers are AGTGGCTTGAAAATGAGCTC (SEQ.ID.NO.:7) and CTTGATCCCTTCTGGTAGATG (SEQ.ID.NO.:8), and they amplify a 327 bp cDNA fragment. These primers were used to test for changes in the KHCS gene expression in several independently isolated populations of human HeLa cells, each selected for spontaneously acquired etoposide resistance, $\beta_2$-microglobulin cDNA sequences were amplified as an internal control. FIG. 16 shows the results of the cDNA-PCR assay on the following populations: CX(0), HeLa population infected with the LNCX vector virus and selected with G418; CX (200), the same cells selected for resistance to 200 ng/ml etoposide; $\Sigma11(O)$, 6(O), and $\Sigma21$ (O), populations obtained after infection of HeLa cells with recombinant retroviruses carrying different GSEs derived from topoisomerase $\alpha$ cDNA, as described in Example 1 of co-pending U.S. patent application Ser. No. 08/033,086, incorporated by reference, and selected with G418:$\Sigma11$ (1000), 6(1000) and $\Sigma21(1000)$, the same populations selected for resistance to 1 µg/ml etoposide. As shown in FIG. 16, the yield of the PCR product specific for the khcs gene was significantly lower in each of the etoposide-selected populations than in the control cells. This result indicates that a decrease in the khcs gene expression is a common natural mechanism for drug resistance.

EXAMPLE 12

Diagnostic Assay

The results presented in the above Examples suggest the utility of diagnostic assays for determining the expression levels of kinesin genes in tumor cells of a cancer patient, relative to a standardized set of cell lines in vitro having well-characterized levels of kinesin heavy chain gene expression correlated with their level of resistance to certain chemotherapeutic drugs such as etoposide. One such standardized set of cell lines comprise the HeLa cell lines described in Example 11. Alternatively, different, tissue-specific standardized set of cell lines are developed by drug selection for each cell type to be evaluated, for example, using human K562 cells for evaluating patients having chronic myelogenous leukemia, or human HL60 cells for patients having acute promyelocytic leukemia.

The assay for kinesin would assess the appropriateness of treatment of human cancer patients with certain anticancer therapeutic regimens. Patients whose tumor cells under-express kinesin may be refractory to treatment with DNA damaging agents, including radiation and the chemotherapeutic drugs etoposide, camptothecin, cisplatin and adriamycin. Such patients, however, may be particularly responsive to treatment with anti-microtubular agents such as colchicine, colcemide, vinblastine, vincristine or vindesine. On the other hand, patients whose tumor cells over-express kinesin, for example, may be responsive to treatment with DNA damaging agents and refractory to treatment with anti-microtubular agents. These assays provide, for the first time, a basis for making such therapeutic judgments before the fact, rather than after a therapeutic regimen has been tried and failed. The assay also provide a basis for determining which patients, previously refractory to treatment with DNA damaging agents, particularly certain anticancer drugs, would benefit from further chemotherapy using anti-microtubular agents, by distinguishing kinesin gene-mediated drug resistance from other mechanism of drug resistance expected to result in cross-resistance to both DNA damaging agents and anti-microtubular drugs.

It should be understood that the foregoing disclosure emphasizes certain specific embodiments of the invention and that all modifications or alternatives equivalent thereto are within the spirit and scope of the invention as set forth in the appended claims.

What is claimed is:

1. A diagnostic assay for determining whether malignant cells in a tumor or a tissue in an animal are sensitive or resistant to DNA damaging chemotherapeutic drugs or agents, the method comprising the steps of
    (a) isolating cellular RNA comprising messenger RNA from malignant cells of a tumor or a tissue from an animal;
    (b) measuring a level of expression of a kinesin gene in the malignant cells of the tumor or tissue;
    (c) determining whether the level of expression of the kinesin gene in the malignant cells of the tumor or tissue indicates that the kinesin gene is over-expressed or under-expressed in the malignant cells of the tumor or tissue in the animal compared with expression of said kinesin gene in non-malignant cells or tissue; and
    (d) providing a diagnosis that malignant cells in said tumor or tissue are resistant to DNA damaging chemotherapeutic drugs or agents when the kinesin gene is under expressed compared with non-malignant cells or tissue or providing a diagnosis that malignant cells in said tumor or tissue are sensitive to DNA damaging chemotherapeutic drugs or agents when the kinesin gene is over-expressed in the tumor or tissue compared with non-malignant cells or tissue.

2. A diagnostic assay for determining whether malignant cells in a tumor or a tissue in an animal are sensitive or resistant to DNA damaging chemotherapeutic drugs or agents, the method comprising the steps of
    (a) isolating cellular protein from malignant cells of a tumor or a tissue from an animal;
    (b) measuring an amount of a kinesin protein in the malignant cells of the tumor or tissue of the animal;
    (c) determining whether the amount of the kinesin protein in the malignant cells of the tumor or tissue indicates that the kinesin gene is over-expressed or under-expressed in the malignant cells of the tumor or tissue in the animal compared with the amount of said kinesin protein in non-malignant cells or tissue; and
    (d) providing a diagnosis that malignant cells in said tumor or tissue are resistant to DNA damaging chemotherapeutic drugs or agents when the amount of kinesin protein is decreased in the tumor or malignant cells compared with non-malignant cells or tissue, or providing a diagnosis that malignant cells in the tumor or tissue are sensitive to DNA damaging chemotherapeutic drugs or agents when the amount of kinesin protein is increased in the malignant cells of the tumor or tissue compared with non-malignant cells or tissues.

3. A diagnostic assay according to claim 1 or 2, wherein the diagnosis is that the malignant cells of the tissue or tumor in the animal will be resistant to an anticancer drug that is a DNA damaging agent where the kinesin gene is under-expressed in the malignant cells of the tumor.

4. A diagnostic assay according to claim 1 or 2, wherein the diagnosis is that the malignant cells of the tissue or tumor in the animal will be susceptible to an anticancer drug that is a DNA damaging agent where the kinesin gene is over-expressed in the malignant cells or tumor.

5. A diagnostic assay for determining whether malignant cells in a tumor or a tissue in an animal are sensitive or resistant to antimicrotubule-directed chemotherapeutic drugs or agents, the method comprising the steps of
    (a) isolating cellular RNA comprising messenger RNA from malignant cells of a tumor or a tissue from an animal;
    (b) measuring a level of expression of a kinesin gene in the malignant cells of the tumor or tissue;
    (c) determining whether the level of expression of the kinesin gene in the malignant cells of the tumor or tissue indicates that the kinesin gene is over-expressed or under-expressed in the malignant cells of the tumor or tissue in the animal compared with expression of said kinesin gene in non-malignant cells or tissue; and
    (d) providing a diagnosis that malignant cells in said tumor or tissue are sensitive to antimicrotubule-directed chemotherapeutic drugs or agents when the kinesin gene is under expressed compared with non-malignant cells or tissue or providing a diagnosis that malignant cells in said tumor or tissue are resistant to antimicrotubule-directed chemotherapeutic drugs or agents when the kinesin gene is over-expressed in the tumor or tissue compared with non-malignant cells or tissues.

6. A diagnostic assay for determining whether malignant cells in a tumor or a tissue in an animal are sensitive or resistant to antimicrotubule-directed chemotherapeutic drugs or agents, the method comprising the steps of
    (a) isolating cellular protein from malignant cells of a tumor or a tissue from an animal;
    (b) measuring an amount of a kinesin protein in the malignant cells of the tumor or tissue of the animal;
    (c) determining whether the amount of kinesin protein in the malignant cells of the tumor or tissue indicates that the kinesin gene is over-expressed or under-expressed in the malignant cells of the tumor or tissue in the animal compared with the amount of said kinesin protein in non-malignant cells or tissue; and (d) providing a diagnosis that malignant cells in said tumor or tissue are sensitive to antimicrotubule-directed chemotherapeutic drugs or agents when the amount of kinesin protein is decreased in the tumor or malignant cells compared with non-malignant cells or tissue, or providing a diagnosis that malignant cells in the tumor or tissue are resistant to antimicrotubule-directed chemotherapeutic drugs or agents when the amount of kinesin protein is increased in the malignant cells of the tumor or tissue compared with non-malignant cells or tissues.

7. A diagnostic assay according to claim 5 or 6, wherein the diagnosis is that the malignant cells of the tissue or tumor in the animal will be resistant to an anticancer drug that is an anti-microtubule agent where the kinesin gene is over-expressed in the malignant cells or tumor.

8. A diagnostic assay according to claim 5 or 6, wherein the diagnosis is that the malignant cells of the tissue or tumor in the animal will be susceptible to an anticancer drug that is an anti-microtubule agent where the kinesin gene is under-expressed in the malignant cells or tumor.

\* \* \* \* \*

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

AATCATCGAT GGATGGATGG          20

(2) INFORMATION FOR SEQ ID NO: 2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 2:

CCATCCATCC ATCGATGATT AAA      23

(2) INFORMATION FOR SEQ ID NO: 3:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 3:

CTTGATCCCT TCTGGTTGAT GCCAGAAGCT CTTCCTGATC CAGCATTTGT ATCTTCAATT    60

TCTCTACCAA TTGGCTTTGT TGGTTAATCT CTTCATCCTT GTCATCAAGT TGTTTATACA    120

ATTTAGCAAG TTCTTCTTCA CACTTTCTTC TTTCAGCATC GGTAAAACTA CCAGCCATTC    180

| | |
|---|---|
| CGACTGCAGC AGCTGGTTTA TCACTGGTAA TAGCAATATC TTTATCCGCT GTGAAGGCTT | 240 |
| CCAAATTAGC TTTCTCTTTG TCAAACTGCT CATCAATAGG CACTGTCTCC CCGTTACGCC | 300 |
| AACGGTTTAG CTCGTTTTCC AGCCACT | 327 |

(2) INFORMATION FOR SEQ ID NO: 4:

(i) SEQUENCE CHARACTERISTICS:
        (A) LENGTH: 2389 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 4:

| | |
|---|---|
| CGACAAACAT CATCTGGGAA GACCCACACG ATGGAGGGTA AACTTCATGA TCCAGAAGGC | 60 |
| ATGGGAATTA TTCCAAGAAT AGTGCAAGAT ATTTTTAATT ATATTTACTC CATGGATGAA | 120 |
| AATTTGGAAT TCATATTAA GGTTTCATAT TTTGAAATAT ATTTGGATAA GATAAGGGAC | 180 |
| TTGTTAGATG TTTCAAAGAC TAACCTTTCA GTCCATGAAG ACAAAAACCG TGTTCCCTAT | 240 |
| GTAAAGGGGT GCACAGAACG TTTCGTGTGT AGTCCAGATG AAGTCATGGA TACCATAGAT | 300 |
| GAAGGGAAAT CCAACAGAGA TGTCGCAGTT ACAAATATGA ATGAACATAG CTCTAGGAGC | 360 |
| CACAGCATAT TTCTTATTAA TGTAAAACAA GAGAATACAC AAACGGAACA GAAACTCAGT | 420 |
| GGAAAGCTTT ATCTGGTTGA TTTAGCTGGC AGTGAGAAGG TTAGTAAGAC TGGGGCTGAA | 480 |
| GGTGCTGTGC TGGATGAAGC TAAGAACATC AAGAAGTCAC TTTCTGCACT TGGAAATGTC | 540 |
| ATTTCTGCTT TGGCAGAGGG CAGTACCTAT GTTCCTTATC GAGATAGTAA AATGACCAGA | 600 |
| ATTCTTCAAG ATTCATTAGG TGGCAACTGT AGGACCACTA TTGTCATATG CTGCTCTCCA | 660 |
| TCATCATACA ATGAGTCTGA GACAAAGTCA ACACTCCTCT TTGGTCAAAG GGCCAAAACA | 720 |
| ATTAAGAACA CAGTCTGTGT CAATGTAGAG TTAACTGCAG AGCAGTGGAA AAAGAAGTAT | 780 |
| GAAAAAGAAA AGGAAAAAAA TAAGACTCTA CGGAACACTA TTCAGTGGCT GGAAAACGAG | 840 |
| CTAAACCGTT GGCGTAACGG GGAGACAGTG CCTATTGATG AGCAGTTTGA CAAAGAGAAA | 900 |
| GCTAATTTGG AAGCCTTCAC AGCGGATAAA GATACTGCTA TTACCAGTGA TAAACCAGCT | 960 |
| GCTGCAGTCG GAATGGCTGG TAGTTTTACC GATGCTGAAA GAAGAAAGTG TGAAGAAGAA | 1020 |
| CTTGCTAAAT TGTATAAACA GCTTGATGAC AAGGATGAAG AGATTAACCA ACAAAGCCAA | 1080 |
| TTGGTAGAGA AATTGAAGAC ACAAATGCTG GATCAGGAAG AGCTTCTGGC ATCAACCAGA | 1140 |
| AGGGATCAAG ATAATATGCA AGCTGAACTG AATCGCCTCC AAGCAGAAAA TGATGCTTCT | 1200 |
| AAAGAAGAAG TCAAAGAAGT TTTACAGGCC TTAGAGGAAC TGGCTGTTAA TTATGATCAG | 1260 |
| AAGTCTCAGG AAGTTGAAGA CAAAACAAAG GAATATGAAT GCTTAGTGA TGAATTGAAT | 1320 |
| CAAAAATCTG CAACTTTAGC AAGTATTGAT GCTGAGCTTC AGAAGCTGAA GGAAATGACC | 1380 |
| AACCACCAGA AGAAACGAGC AGCTGAAATG ATGGCATCAT TATTAAAAGA CCTTGCAGAA | 1440 |
| ATAGGAATTG CTGTGGGGAA TAACGATGTG AAGCAACCAG AAGGAACTGG TATGATAGAT | 1500 |
| GAAGAGTTTA CTGTTGCAAG ACTCTACATT AGCAAAATGA AATCAGAAGT AAAGACCATG | 1560 |
| GTGAAACGCT GCAAACAGCT AGAAAGCACG CAGACTGAGA GCAACAAAAA AATGGAAGAA | 1620 |
| AATGAGAAAG AGTTAGCAGC ATGCCAGCTT CGGATCTCCC AACATGAAGC CAAAATCAAG | 1680 |
| TCACTGACTG AGTACCTTCA GAATGTAGAA CAAAAGAAGA GGCAGCTGGA GGAATCTGTT | 1740 |

-continued

```
GATTCCCTTG GTGAGGAGCT AGTCCAACTC CGAGCACAAG AGAAAGTCCA TGAAATGGAA    1800

AAAGAGCACT TGAACAAGGT TCAGACTGCA AATGAAGTCA AGCAAGCTGT TGAGCAGCAG    1860

ATCCAGAGTC ACAGAGAAAC CCACCAAAAA CAAATCAGTA GCTTGCGAGA TGAAGTTGAG    1920

GCAAAGGAAA AGCTAATCAC TGACCTCCAA GACCAAAACC AGAAGATGGT GTTGGAGCAG    1980

GAACGGCTAA GGGTGGAGCA TGAGAGGCTG AAGGCTACAG ACCAAGAGAA GAGCAGGAAG    2040

CTGCATGAGC TCACGGTTAT GCAAGACAGA CGAGAACAAG CAAGACAAGA CTTGAAGGGT    2100

TTGGAGGAGA CCGTGGCAAA AGAACTTCAG ACTTTACACA ACCTGCGTAA GCTCTTTGTT    2160

CAGGACTTGG CTACCAGGGT GAAAAGAGG CCGAGGTCGA CTCTGACGAC ACTGGCGGCA    2220

GTGCTGCACA GAAGCAGAAA ATCTCCTTCC TTGAAAACAA CCTTGAACAG CTCACCAAAG    2280

TGCACAAGCA GTTGGTACGT GATAATGCAG ATCTTCGCTG TGAGCTTCCT AAGTTAGAGA    2340

AACGGCTTAG AGCTACTGCA GAAAGAGTGA AAGCTTTGGA GTCAGCCCG              2389
```

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

```
CTCCCAAGCT TATGGATGGA TG                                              22
```

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 6:

```
CATCCATCCA TAAGCTTGGG AGAAA                                           25
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 7:

```
TGAGTGAGTG AATCGATGAT TAAA                                            24
```

(2) INFORMATION FOR SEQ ID NO: 8:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 8:

AATCATCGAT TCACTCACTC A                                              21
```